United States Patent [19]

Hanauske-Abel et al.

[11] Patent Number: 5,849,587

[45] Date of Patent: Dec. 15, 1998

[54] METHOD OF INHIBITING VIRAL REPLICATION IN EUKARYOTIC CELLS AND OF INDUCING APOPTOSIS OF VIRALLY-INFECTED CELLS

[75] Inventors: Hartmut M. Hanauske-Abel, Edgewater; Robert Walter Grady, Kinnelon, both of N.J.; Axel Hanauske, Wolratshausen, Germany; Linda Andrus, New York, N.Y.; Paul Szabo, Linden, N.J.

[73] Assignee: Cornell Research Foundation, Inc., Ithaca, N.Y.

[21] Appl. No.: 488,811

[22] Filed: Jun. 9, 1995

[51] Int. Cl.$^6$ ........................................... C12N 5/08
[52] U.S. Cl. .................. 435/372.3; 435/375; 514/185
[58] Field of Search ..................................... 514/348, 634, 514/185; 435/372, 372.3, 375

[56] References Cited

U.S. PATENT DOCUMENTS

| | | | |
|---|---|---|---|
| 4,246,266 | 1/1981 | Undheim et al. | 514/348 |
| 4,585,780 | 4/1986 | Hider et al. | 514/348 |
| 4,840,958 | 6/1989 | Hider et al. | 514/348 |
| 4,908,371 | 3/1990 | Moerker et al. | 514/318 |
| 5,185,352 | 2/1993 | Aranda et al. | 514/348 |
| 5,256,676 | 10/1993 | Hider et al. | 514/348 |
| 5,262,409 | 11/1993 | Margolis et al. | 514/183 |
| 5,344,846 | 9/1994 | Jakus et al. | 514/634 |
| 5,399,566 | 3/1995 | Katano et al. | 514/340 |

FOREIGN PATENT DOCUMENTS

GB 2 146 989
A  5/1985  European Pat. Off. .
WO 92/05190  4/1992  WIPO .

OTHER PUBLICATIONS

Herahko et al., "Results of Long–Term Deferiprone (LI) Therapy," *Blood*, (1994) (abstract).
Abbruzzese, A. et al. Biochim. et Biophys. Acta 1991. pp. 159–166.
Mitsuya, H. et al. 1990 Science vol. 249 pp. 1533–1544.
Park, M. H. et al. 1993 Biofactors vol. 4 (2) pp. 95–104.
Hashiguchi, et al., "Inhibition of Two Copper–Containing Enzymes, Tyrosinase and Dopamine β–Hydroxylase, by L–Mimosine," *Molecular Pharmacology*, 13(2):362–367 (1977).
McCaffrey et al., "Specific Inhibition of eIF–5A and Collagen Hydroxylation by a Single Agent: Antiproliferative and Fibro–suppressive Effects on Smooth Muscle Cells from Human Coronary Arteries," *Journal of Clinical Investigation*, 95:446–455 (1995).

*Primary Examiner*—Nancy Degen
*Assistant Examiner*—Irem Yucel
*Attorney, Agent, or Firm*—Nixon, Hargrave, Devans & Doyle LLP

[57] ABSTRACT

The present invention is directed to methods which employ inhibition of the post-translational hypusine formation in the intracelluar protein eIF-5A, for the purpose of suppressing infections by viruses that parasitize eIF-5A so as to promote their own replication. Intentional inhibition of the post-translational formation of hypusine in infected host cells with compounds generically termed 'hypusine inhibitors' not only selectively suppresses the production of viral proteins and of infectious viral particles, but also causes, particularly after hypusine inhibitor withdrawal, apoptosis in such virally-infected cells. Each of these methods, respectively, involves administering, to eukaryotic cells, tissues, or individuals, an agent which blocks the post-translational intracellular formation of hypusine, in an amount sufficient to: suppress biosynthesis of bioactive eIF-5A, suppress translational interaction of eIF-5A with viral elements of nucleic acid and/or protein structure, inhibit biosynthesis of viral proteins of Rev-dependent lentiviruses or of viruses dependent on interaction of eIF-5A with viral elements of nucleic acid and/or protein structure, inhibit replication of Rev-dependent lentiviruses or of viruses dependent on interaction of eIF-5A with viral elements of nucleic acid and/or protein structure, and induce apoptosis of virally-infected cells. This agent can be a compound of Formulae I or II and derivatives thereof as follows:

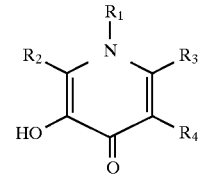

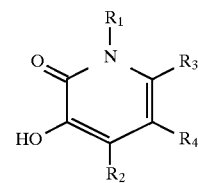

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

61 Claims, 15 Drawing Sheets

METHOD OF INHIBITING VIRAL REPLICATION IN EUKARYOTIC CELLS AND OF INDUCING APOPTOSIS OF VIRALLY-INFECTED CELLS

This invention was made with the assistance of the U.S. Government which, as a result, may have certain rights in the invention.

FIELD OF THE INVENTION

The present invention relates to a method of inhibiting viral replication in eukaryotic cells and of inducing apoptosis of virally infected cells.

BACKGROUND OF THE INVENTION

Recently, a group of viruses of major epidemiologic and economic importance was identified that shares the strict requirement for a specific regulator (protein and/or nucleic) in order to express the genes encoding their structural proteins for core and capsid formation. Hence, the specific regulator determines efficient propagation, production of infectious progeny, and the establishment productive infection. The major representative of this group is the human immunodeficiency virus type 1 ("HIV-1"), the agent causing AIDS. The specific regulator (protein and/or nucleic acid) that strictly controls the expression of the structural proteins in HIV-1 is the Rev/RRE system. Rev designates a protein and stands for "regulator of virion expression", while RRE is the abbreviation for "Rev response element" and designates a particular, known sequence of the viral RNA that interacts with Rev in a highly specific manner. Mutational deficiencies in either the Rev or the RRE element of this specific regulator invariably compromise or abolish replicative competence of HIV-1 [See, for instance: Gallo et al., *The Human Retroviruses*, Academic Press 69–106 (1991); Malim et al., *Mol. Cell. Biol.* 13:6180–6189 (1993); and Mann et al., *J. Mol. Biol.* 241:193–207 (1994), which are hereby incorporated by reference]. Such replication-incompetent HIV-1 systems have been used widely in complementation assays to study whether the specific regulators of other viruses can compensate for a defective Rev/RRE system. Using this technique, it was shown that, for instance, certain elements of the Mason-Pfizer virus can render HIV-1 expression and replication Rev-independent [Bray et al., *Proc. Natl. Acad. Sci. USA* 91:1256–1260 (1994), which is hereby incorporated by reference]. Similar functional complementation was achieved with the human immunodeficiency virus type 2 and with the human T-cell leukemia viruses type 1 and 2 [Lewis et al., *J. Virol.* 64:1690–1697 (1990); Ahmed et al., *Gen. Develop.* 4:1014–1022 (1990); Rimsky et al., *Nature* 335:738–740 (1988), which are hereby incorporated by reference] as well as with hepatitis B virus [Hope et al., *J. Cell. Biochim. Supplement* 21B:192 (1995), which is hereby incorporated by reference] and simian immunodeficiency virus [Zolotokhin et al., *J. Virol.* 68:7944–7952 (1994), which is hereby incorporated by reference]. Within this group of viruses, transcomplemenatation is reciprocal, e.g. Rev of HIV-1 complements incompetent simian immunodeficiency virus and is established for viral replication systems other than HIV-1, e.g., the Rev-equivalent protein of human T-cell leukemia virus type 1 complements incompetent simiam immunodeficiency virus [Krohn et al., *J. Virol.* 67:5681–5684 (1993), which is hereby incorporated by reference]. In addition, structural studies revealed the presence of Rev-like proteins in feline immunodeficiency virus, equine infectious anemia virus [Manusco et al., *J. Virol.* 68:1998–2001 (1994), which is hereby incorporated by reference], and caprine arthritis encephalitis virus [Schoborg et al., *Virology* 202:1–15 (1994), which is hereby incorporated by reference], further attesting to the well-established structural and functional relationship among the retroviruses. The visna virus and the bovine immunodeficiency virus also are Rev-dependent and belong to this group of transcomplementable viruses that show a strict requirement for a specific regulator in order to express the genes encoding their structural proteins for core and capsid [Toohey et al., *Virology* 200:276–280 (1994) and Oberste et al., *J. Virol.* 67:6395–6405 (1993), which are hereby incorporated by reference]. It must be anticipated that assignments of viral species to this group will significantly increase.

In view of the seriousness of the AIDS epidemic and the lack of an effective treatment, the need exists for development of new therapies for treating AIDS and related viruses. The present invention is directed toward overcoming this deficiency in the art.

SUMMARY OF THE INVENTION

The present invention is directed to methods of inhibiting the post-translational formation of the genetically non-coded residue hypusine [i.e. N $^\epsilon$-(4-amino-2(R)-hydroxybutyl)-L-lysine] within the cellular protein eukaryotic initiation factor-5A ("eIF-5A"). More particularly, the present invention involves inhibiting intracellular synthesis of functional bioactive eIF-5A, inhibiting the translationally productive interaction of eIF-5A with viral elements of nucleic acids and/or protein structure, inhibiting biosynthesis of viral proteins of Rev-dependent lentiviruses or of viruses dependent on interaction of eIF-5A with viral elements of nucleic acid and/or protein structure, and inhibiting replication of Rev-dependent lentiviruses or viruses dependent on interaction of eIF-5A with viral elements of nucleic acid and/or protein structure. These methods, respectively, involve administering, to eukaryotic cells, tissues, or individuals, an agent which blocks the post-translational intracellular formation of hypusine in an amount sufficient to suppress biosynthesis of bioactive eIF-5A where the agent is a deoxyhypusyl hydroxylase inhibitor, in an amount sufficient to suppress the translationally productive interaction of eIF-5A with viral elements of nucleic acid and/or protein structure, in an amount sufficient to inhibit biosynthesis of viral proteins of Rev-dependent lentiviruses or of viruses dependent on interaction of eIF-5A with viral elements of nucleic acid and/or protein structure, and in an amount sufficient to inhibit replication of Rev-dependent lentiviruses or of viruses dependent on interaction of eIF-5A with viral elements of nucleic acid and/or protein structure.

Another aspect of the present invention involves inducing apoptosis in eukaryotic cells infected with Rev-dependent lentiviruses or viruses dependent on interaction of host cell eIF-5A with viral elements of nucleic acid and/or protein structure. This is achieved by administering an agent to eukaryotic cells which blocks the post-translational intracellular formation of hypusine in an amount sufficient to induce apoptosis of virally-infected cells.

This agent can be a compound of Formulae I or II and derivatives thereof as follows:

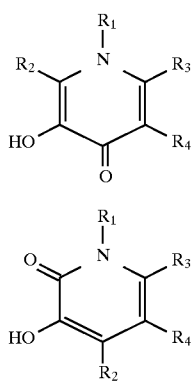

R$_1$, R$_2$, R$_3$, and R$_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

BRIEF DESCRIPTION OF THE DRAWINGS

FIG. 11A displays PMA-induced/untreated cells actively engaged in production of infectious HIV-1 particles, which are budding from the cytoplasmic membranes and clearly discernible in the extracellular space.

DETAILED DESCRIPTION OF THE INVENTION AND THE DRAWINGS

Figure 1:
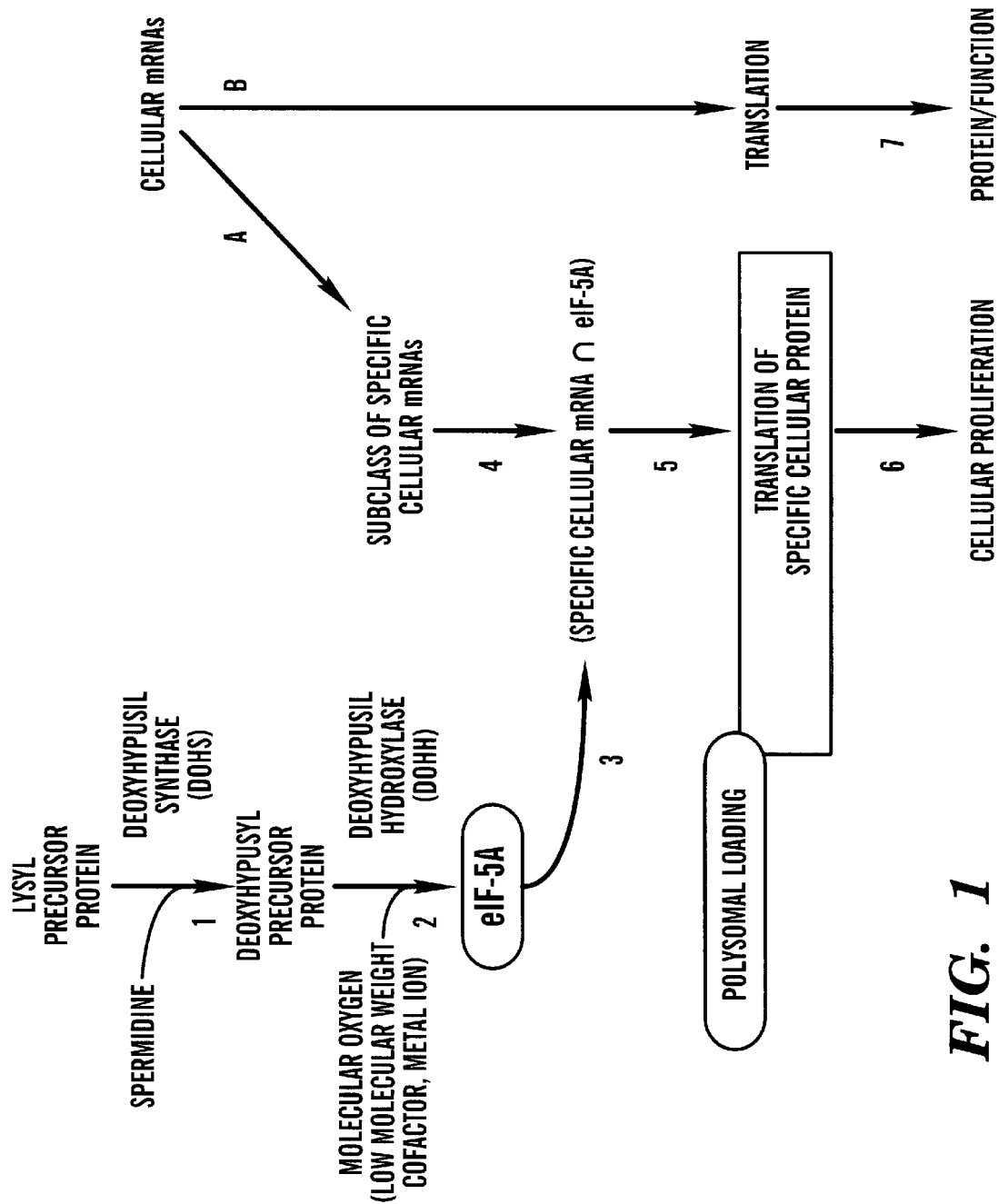
FIG. 1 is a schematic drawing which depicts the stepwise post-translational formation of the hypusine [i.e. N$^\epsilon$-(4-amino-2(R)-hydroxybutyl)-L-lysine] residue of the protein eIF-5A, involving the enzymes deoxyhypusyl synthase ("DOHS") (See 1) and deoxyhypusyl hydroxylase ("DOHH") (See 2) in a sequential manner. It illustrates the physiological function of eIF-5A, the only protein that is presently known to contain hypusine. Once hypusine is formed, eIF-5A physically interacts (See 3 and 4) with a small subclass of cellular mRNAs, indicated by A, of the total cellular mRNAs. In this way, eIF-5A enables the preferential polysomal loading of such mRNAs (See 5) and their translation into proteins (See 6). These proteins, in turn, have been shown to be essential for irreversibly engaging the multi-component machinery that initiates replication of eukaryotic cells. Translation of the vast majority of cellular mRNAs, indicated by B, and "household" protein biosynthesis proceed independent of hypusine formation and the eIF-5A pathway (See 7).

The present invention is directed to methods of inhibiting the post-translational formation of the genetically non-coded residue hypusine [i.e. $N^\epsilon$-(4-amino-2(R)-hydroxybutyl)-L-lysine] within the cellular protein eukaryotic initiation factor-5A ("eIF-5A"). More particularly, the present invention involves inhibiting intracellular synthesis of functional bioactive eIF-5A, inhibiting the translationally productive interaction of eIF-5A with viral elements of nucleic acids and/or protein structure, inhibiting biosynthesis of viral proteins of Rev-dependent lentiviruses or of viruses dependent on interaction of eIF-5A with viral elements of nucleic acid and/or protein structure, and inhibiting replication of Rev-dependent lentiviruses or viruses dependent on interaction of eIF-5A with viral elements of nucleic acid and/or protein structure. These methods, respectively, involve administering, to eukaryotic cells, tissues, or individuals, an agent which blocks the post-translational intracellular formation of hypusine in an amount sufficient to suppress biosynthesis of bioactive eIF-5A where the agent is a deoxyhypusyl hydroxylase inhibitor, in an amount sufficient to suppress the translationally productive interaction of eIF-5A with viral elements of nucleic acid and/or protein structure, in an amount sufficient to inhibit biosynthesis of viral proteins of Rev-dependent lentiviruses or of viruses dependent on interaction of eIF-5A with viral elements of nucleic acid and/or protein structure, and in an amount sufficient to inhibit replication of Rev-dependent lentiviruses or of viruses dependent on interaction of eIF-5A with viral elements of nucleic acid and/or protein structure.

Another aspect of the present invention involves inducing apoptosis in eukaryotic cells infected with Rev-dependent lentiviruses or viruses dependent on interaction of host cell eIF-5A with viral elements of nucleic acid and/or protein structure. This is achieved by administering an agent to eukaryotic cells infected with Rev-dependent lentiviruses or of viruses dependent on interaction of eIF-5A with viral elements of nucleic acid and/or protein structure which blocks the post-translational intracellular formation of hypusine in an amount sufficient to induce apoptosis of virally-infected cells.

As described in the "Background of the Invention" Section of this application, a group of viruses of major epidemiologic and economic importance, which are typified by the human immunodeficiency virus type 1 (HIV-1), share the strict requirement for a specific regulator (i.e. protein and/or nucleic acid) in order to express viral structural genes and, hence, to propagate efficiently and produce infectious progeny. In addition to the human immunodeficiency viruses, this group consists of, but is not not limited to, human T-cell leukemia viruses, hepatitis B virus, visna virus, simian immunodeficiency viruses, bovine immunodeficiency virus, equine infectious anemia virus, feline immunodeficiency viruses, caprine arthritis-encephalitis virus, and Mason-Pfizer virus. Reference to HIV-1 is used here only to exemplify the function of this specific regulator, to delineate its interaction with host cell eIF-5A, and to demonstrate the methods of this invention as they are applied to interfere with this specific regulator and render it nonfunctional.

After viral infection of human cells by HIV-1, the viral genomic RNA is transcribed into DNA and subsequently incorporated into the human genome. Upon transcription, only the completely spliced about 2-kb transcripts encoding the HIV-1 proteins, Tat, Rev, and Nef, or Tat-Rev fusion proteins, are exported to the cytoplasm for efficient translation by the protein producing machinery of the host cell. The incompletely spliced about 4-kb and the unspliced about 9-kb viral transcipts are not themselves exported and, thereby, fail to gain productive access to this machinery, apparently due to control mechanisms that in eukaryotes generally deny translation of incompletely spliced and unspliced RNA. This failure to be exported, apparently due to lack of nucleocytoplasmic transport and/or polysomal translation, is of grave consequence to the replicative ability of HIV-1 and severely limits production of new virions. Not only are all the structural proteins of the HIV-1 particle encoded by these incompletely/unspliced transcripts, but the about 9-kb species also constitutes the infectious viral genome to be packaged into these particles. It is the function of the Rev protein, the specific regulator of HIV-1, to enter into the nucleus after being synthesized on cytoplasmic host cell polysomes, to bind to the Rev-response element ("RRE") of the about 4-kb and about 9-kb transcripts, and, thereby, to convey them to the protein producing machinery of the host cell for effective biosynthesis of the viral proteins, Gag, Pol, Vif, Vpr, Vpu, and Env.

Rev is known to bind to the eIF-5A of infected host cells [Ruhl et al., *J. Cell. Bio.* 123, 1309–1320 (1993), which is hereby incorporated by reference]. As depicted in FIG. 1, eIF-5A is the critical element in a proposed pathway to provide preferential polysomal access to a subclass of specific cellular mRNAs which encode proteins that enable and coordinate DNA replication, i.e., initate cellular proliferation. eIF-5A is unique in that it is the only protein known to containing a lysine-derived hypusine [Nε-(4-amino-2(R)-hydroxybutyl)-L-lysine] residue which is formed post-translationally by the enzymes deoxyhypusyl synthase ("DOHS") (See 1) and deoxyhypusyl hydroxylase ("DOHH") (See 2). Once hypusine is formed, eIF-5A physically interacts (See 3 and 4) with a small subclass, indicated by A, of the total cellular mRNAs; this subset has been termed "hypusine-dependent messenger nucleic acids", or hymns [Hanauske-Abel et al., FEBS Lett. 366, 92–98 (1995), which is hereby incorporated by reference]. In this way, eIF-5A enables preferential polysomal loading of the estimated only about 120 different mRNAs of the hymn type (See 5) and directly entitles them to translation (See 6), bypassing the need to "wait in line" until ribosomes become available. The hymn-encoded proteins, in turn, are essential for irreversibly engaging the multi-component machinery that initiates replication of eukaryotic cells [Hanauske-Abel et al., FEBS Lett. 366, 92–98 (1995), which is hereby incorporated by reference]. Translation of the vast majority of cellular mRNAs, estimated to reach over 20,000 distinct species per cells and indicated by B, is bypassed (compare 6 and 7). The routine translation of all these mRNAs constitutes the usual mechanism for "household" protein biosynthesis and proceeds independent of hypusine formation and the eIF-5A pathway (See 7).

Figure 2:
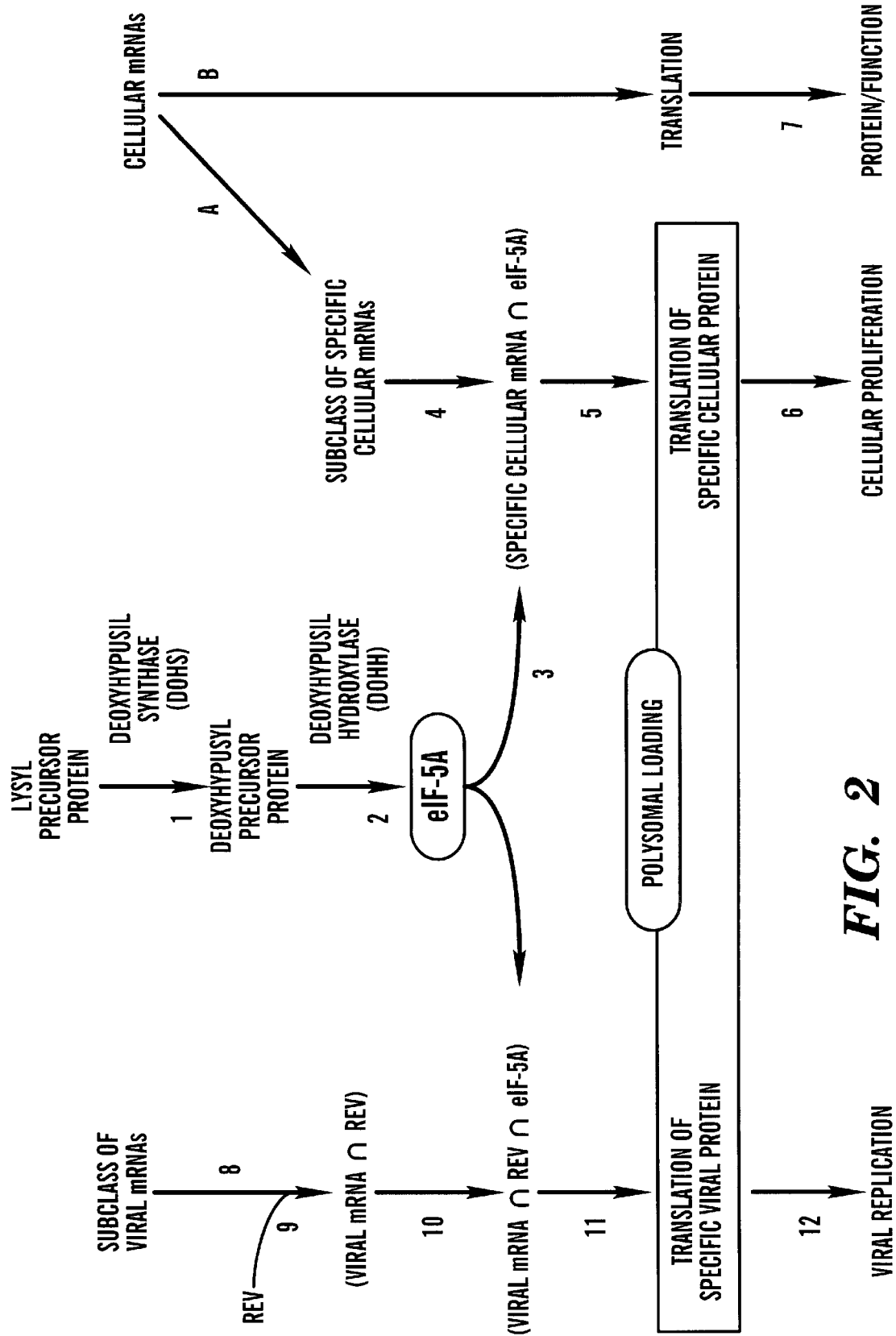
FIG. 2 is a schematic drawing which depicts the manner in which the eIF-5A pathway becomes parasitized by the human immunodeficiency virus type 1 (i.e. HIV-1), a representative example of the class of viruses that, after penetration into eukaryotic cells, feed on the eIF-5A pathway to achieve preferential translation of viral proteins and thus, gain a generative advantage. A subclass of viral mRNAs (See 8), encoding in particular the structural proteins that form the virion core and capsid, interacts with the viral protein Rev (See 9) through a specific nucleotide sequence, the Rev response element ("RRE"). It is the Rev component of this complex (See 10) which generally is assumed to interact specifically with host cell eIF-5A. As a result, these RRE-containing viral mRNA species, which otherwise would show very limited or no translational efficiency, become eligible for preferential polysomal loading and translation (See 11). In this manner, the production of key viral proteins for virion formation and packaging is assured and viral replication guaranteed (See 12). Production of Rev at the host cell polysomes is known to occur independent of RRE, Rev, and eIF-5A.

As shown in FIG. 2, the eIF-5A pathway of FIG. 1 can be parasitized by the human immunodeficiency virus type 1 ("HIV-1") [Ruhl et al., *J. Cell. Biol.* 123, 1309–1320 (1993), which is hereby incorporated by reference]. HIV-1 now is being recognized as a representative example of the class of viruses that, after penetration into eukaryotic cells, feed on the eIF-5A pathway to achieve preferential translation of viral structural proteins and thus, gain a generative advantage. The outline provided in FIG. 2 is compatible with the finding that HIV-1 multiplication occurs preferentially in proliferating cells, particularly of the T-cell lineage [see, for instance, Gowda et al., *J. Immunol.* 142, 773–780 (1989) or Klatzmann et al., *Immunol. Today* 7, 291–296 (1986), and references therein, all of which are hereby incorporated by reference], and is compatible with the finding that efficient HIV replication in human peripheral blood mononucleolar cells and in human T-cell lines correlates with eIF-5A expression [Bevec et al., *Proc. Natl. Acad. Sci. USA* 91, 10829–10833 (1994), which is hereby incorporated by reference]. A subclass of viral mRNAs (See 8) encoding in particular the structural proteins that form the virion core and capsid, interacts with the viral protein Rev (See 9) through a specific nucleotide sequence, the Rev response element ("RRE"). The Rev/RRE unit constitutes the specific regulator for biosynthesis of HIV-1 proteins [see, for instance, Gallo et al., *The Human Retroviruses,* 69–106, Academic Press (1991), which is hereby incorporated by reference]. It is the Rev component of this complex (See 10) which specifically interacts with host cell eIF-5A [Ruhl et al., *J. Cell. Biol.* 123, 1309–1320 (1993), which is hereby incorporated by reference]. As a result, these RRE-containing viral mRNA species, which otherwise would show very limited or no translational efficiency, become eligible for preferential polysomal loading and translation (See 11), resulting in active production of infective HIV-1 virions. In this manner, the production of key proteins for virion formation and packaging is assured and viral replication guaranteed (See 12). Production of Rev at the host cell polysomes is known to occur independent of RRE, Rev, and eIF-5A.

Figure 3:
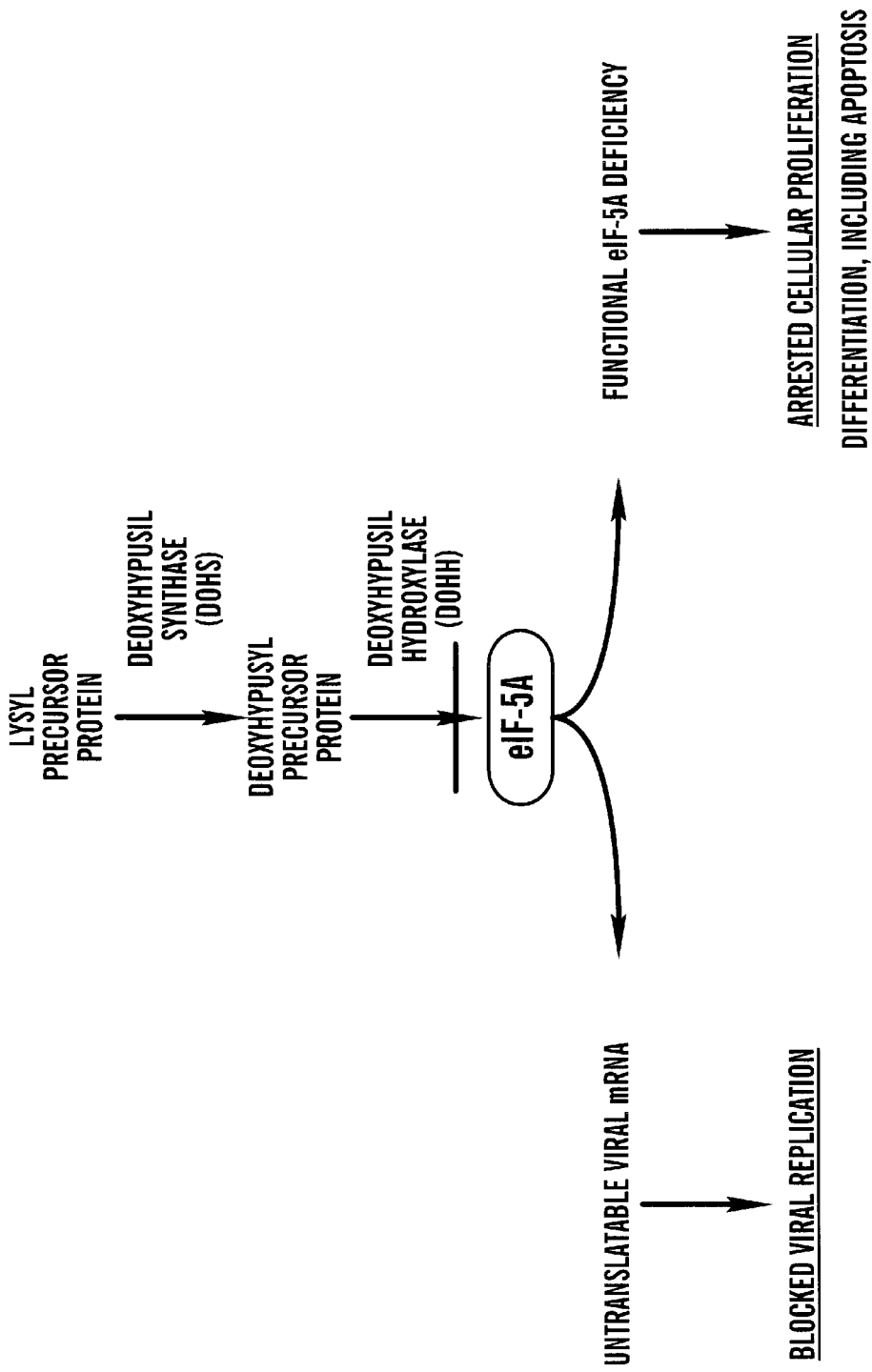
FIG. 3 is a schematic drawing which, in accordance with the present invention, depicts the effect of a hypusine inhibitor on viral replication and cell proliferation. Processing of viral mRNA is markedly affected by lack of bioactive eIF-5A due to suppression of DOHH and results in blocked viral replication. Lack of bioactive eIF-5A is known also to arrest cellular proliferation. In response to any kind of arrest of proliferation, cells are generally known to be able to activate genetically pre-programmed mechanisms which impart novel biological properties. In certain cells, these novel properties are well known to include the engagement of self-destructive activities ("apoptosis"). This induction of apoptosis can be utilized to clear out large segments of the HIV-1 producing cell population.

FIG. 3 provides a conceptual outline which in accordance with the present invention, depicts the effect of a hypusine inhibitor, acting at the level of DOHH, on viral replication and cell proliferation. Processing of viral mRNA should be markedly affected by lack of bioactive eIF-5A due to suppression of DOHH, and should result in blocked viral replication. Intentional interference with the post-translational modifications of eIF-5A, especially at the level of DOHH, was found to compromise severely the role of the eIF-5A pathway in cellular proliferation in a critical manner [Hanauske-Abel et al., *Biochim. Biophys. Acta* 1221, 115–124 (1994), which is hereby incorporated by reference]. In response to any kind of arrest of proliferation, cells are generally known to be able to activate genetically pre-programmed mechanisms which impart novel biological properties ("proliferation-differentiation switch") [see, for instance, Pardee, *Science* 246, 603–608 (1989) and Olson, *Dev. Biol.* 154, 261–272 (1992), which are hereby incorporated by reference]. In certain cells, particularly in those infected with virus, these novel properties are proposed to include the hypusine inhibitor-induced initiation of auto-destructive activities ("apoptosis") which, in turn, may lead to the rapid suicide of large segments of the HIV-1 producing cell population. Thus, when in accordance with the present invention, DOHH inhibitors are applied to treat infections caused by viruses that require a specific regulator (Rev or a functional equivalent) to express viral structural genes for efficient replication, the intentional interference with said post-translational modifications of EIF-5A will result in pharmacologically induced Rev deficiency due to hypusine inhibition/eIF-5A failure, and thus will cause two distinct effects: i) blocked viral replication, and ii) arrested cellular proliferation, the latter triggering differentiation, including irreversible auto-destruction of a large segment of the virally-infected cells (FIG. 3).

Thus, the compounds of the present invention prevent replication of viruses that require a specific regulator (i.e. Rev or a functional equivalent), and, perhaps more importantly, these chemicals are able to trigger cells already infected to activate pre-programmed suicide mechanisms. This combination of effects will clearly have a major impact on arresting HIV-1 by dramatically decreasing viral load, which is the single most decisive determinant of immune system failure in AIDS patients. Consequently, these compounds should allow the immune system to cope more effectively with residual virus.

The agent of the present invention can be a compound of Formulae (I) or (II) and derivatives thereof as follows:

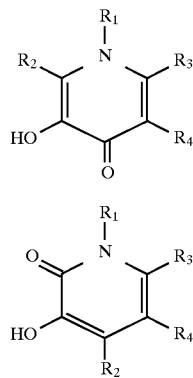

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

The alkyl, alkenyl, alkoxy, aryl, aralkyl, and cycloalkyl groups represented by $R_1$, $R_2$, $R_3$, and $R_4$ can be substituted or unsubstituted. Examples of unsubstituted alkyl groups are methyl, ethyl, propyl, isopropyl, butyl, sec-butyl, pentyl, hexyl, and the like. Unsubstituted alkenyl groups can be 2-propenyl, 2-butenyl, 3-butenyl, 2-methyl-2-butenyl, and the like. Unsubstituted alkoxy groups can be methoxy, ethoxy, propoxy, sopropoxy, and the like. Unsubstituted aryl groups can be phenyl or naphthyl. Aralkyl groups can be, for example, benzyl and phenylethyl. Cycloalkyl groups can be cyclopentyl, cyclohexyl, 4-methyl cyclohexyl, and the like. For substituted alkyl, alkenyl, alkoxy, aryl, aralkyl, and cycloalkyl groups, substituents can include, for example, halo, alkoxy, amino, hydroxy, carboxy, carboalkoxy, and carbamyl. Aryl and aralkyl groups can, in addition, contain alkyl substituents.

The post-translational hydroxylations of the hydroxylation-dependent proteins, such as the intracellular eIF-5A or the extracellular collagens, occur within highly specific motifs of their primary structure. For example, these motifs are -G-x-m*-G- for prolyl 4-hydroxylase, -G-m*-x-G- for deoxyhypusyl hydroxylase, and -C-x-m*-x(4)-[F/Y]-x-C-x-C- for aspartyl/asparaginyl hydroxylase, with m* indicating the position of the substrate residue to be modified by hydroxylation, i.e. prolyl, deoxyhypusyl, or aspartyl/asparaginyl, respectively, G being glycine, x indicating the presence of any residue, C being cysteine, F being phenylalanine, and Y being tyrosine. It is generally accepted that all protein hydroxylases, when hydroxylating artificial substrates consisting solely of the appropriate motifs, as defined above, show low or very low affinity for such substrates. This is attributed to the fact that these short motifs do not present themselves to the active site of the enzymes in the conformation known to be optimal for hydroxylation, a conformation easily assumed, however, within the structure of a larger peptide or the native substrate protein. To overcome this lack of affinity, suitable peptide motifs or their corresponding peptidomimetics, termed 'carriers', can be equipped with a reactive moiety, termed 'warhead', that is precisely positioned to interact with the active site metal ion common to all these protein hydroxylases. Directed to the enzyme of interest by the appropriate, protein hydroxylase-specific carrier, the warhead interacts with the active site metal, locking the carrier to the enzyme and, in this manner, enhances the inhibitory capacity of the carrier which otherwise might be either non- or only weakly inhibitory. This concept, termed "warhead strategy", is applicable to the rational design of all substrate motif-guided protein hydroxylase inhibitors. As to Formulae (I) and (II), such a warhead strategy is effected where $R_1$, $R_2$, $R_3$, and/or $R_4$ is a peptide or peptidomimetic moiety containing 10 to about 30 carbon atoms. The warhead strategy requires that the warheads, which may themselves be inhibitory for the protein hydroxylases, must fit their respective active sites and must be reasonably stable under biological conditions, e.g., not susceptible to redox cycling. Consequently, warheads can consist of moieties of Formulae (I) or (II), for instance, properly positioned on a suitable carrier for optimal anti-viral effect.

Table I contains representative forms of the hydroxypyridone compounds of Formula (I) of the present invention:

TABLE I

| Trivial name | | $R_1$ | $R_2$ | $R_3$ | $R_4$ |
|---|---|---|---|---|---|
| I | L-mimosine | —CH$_2$CH(COOH)NH$_2$ | H | H | H |
|   | HK-1, CP20, L1, DMHP | —CH$_3$ | —CH$_3$ | H | H |

TABLE I-continued

| Trivial name | $R_1$ | $R_2$ | $R_3$ | $R_4$ |
|---|---|---|---|---|
| HK-2, CP94 | —CH$_2$CH$_3$ | —CH$_2$CH$_3$ | H | H |
| CP93 | —CH$_3$ | —CH$_2$CH$_3$ | H | H |
| CP96 | —(CH$_2$)$_2$OCH$_3$ | —CH$_2$CH$_3$ | H | H |
| HK-26, CP21 | —CH$_2$CH$_3$ | —CH$_3$ | H | H |
| HK-27, CP22 | —(CH$_2$)$_2$CH$_3$ | —CH$_3$ | H | H |
| HK-16 | —CH$_2$CH=CH$_2$ | —CH$_3$ | H | H |
| CP23 | —CH$_2$(CH$_3$)$_2$ | —CH$_3$ | H | H |
| CP40 | —(CH$_2$)$_2$OH | —CH$_3$ | H | H |
| CP41 | —(CH$_2$)$_3$OH | —CH$_3$ | H | H |
| CP42 | —(CH$_2$)$_4$OH | —CH$_3$ | H | H |
| CP43 | —(CH$_2$)$_5$OH | —CH$_3$ | H | H |
| CP44 | —(CH$_2$)$_2$NH$_2$ | —CH$_3$ | H | H |
| HK-15, CP51 | —(CH$_2$)$_2$OCH$_3$ | —CH$_3$ | H | H |
| CP54 | —CH(CH$_3$)CH$_2$OCH$_3$ | —CH$_3$ | H | H |
| CP52 | —(CH$_3$)$_3$OCH$_2$CH$_3$ | —CH$_3$ | H | H |
|  | —CH$_3$ | H | —CH$_3$ | H |
|  | —CH$_3$ | H | H | —CH$_3$ |
|  | —CH$_2$CH(COOC$_2$H$_5$)NH$_2$ | H | H | H |

Table II contains representative structures of the hydroxy-pyridone compounds of Formula (II) of the present invention:

TABLE II

|  | $R_1$ | $R_2$ | $R_3$ | $R_4$ |
|---|---|---|---|---|
| II | —CH$_3$ | —CH$_3$ | H | H |
|  | —CH$_2$CH$_3$ | —CH$_2$CH$_3$ | H | H |
|  | —CH$_3$ | —CH$_2$CH$_3$ | H | H |
|  | —(CH$_2$)$_2$OCH$_3$ | —CH$_2$CH$_3$ | H | H |
|  | —CH$_2$CH$_3$ | —CH$_3$ | H | H |
|  | —(CH$_2$)$_2$CH$_3$ | —CH$_3$ | H | H |
|  | —CH$_3$ | H | —CH$_3$ | H |
|  | —CH$_3$ | H | H | —CH$_3$ |

Compounds of Formula (I)

Compounds of Formula (I) are synthesized by one of several general procedures.

Method A

This method is adapted from Kontoghiorghes and Sheppard (*Inorg. Chim. Acta* 136:L11–L12 (1987)), which is hereby incorporated by reference. In brief, a 3-hydroxy-4-pyrone is refluxed for approximately 6 hours with three equivalents of a primary amine dissolved in an appropriate solvent. The reaction mixture is decolorized with charcoal, filtered, and the filtrate evaporated to give a dark residue. The residue is recrystallized from one to three times from an appropriate solvent to yield a solid product with a narrow melting point and an NMR spectrum consistent with the structure anticipated.

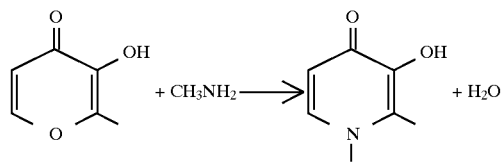

In particular, 3-hydroxy-2-methyl-4-pyrone (10 g) was refluxed for 6.5 hours with three equivalents of aqueous methylamine (40%) in 200 ml of water. The reaction mixture was allowed to cool after which decolorizing charcoal was added to the solution, and the mixture was stirred for 0.5 hours. After filtration, the solvent was evaporated under reduced pressure, and the solid residue recrystallized three times from water to yield 1,2-dimethyl-3-hydroxypyrid-4-one (HK-1, L1, CP20, DMHP) as fine white needles.

In a slight modification of this procedure, N-carboxymethyl-3-hydroxy-2-methylpyrid-4-one is prepared as described by Zhang et al., *Can. J. Chem.* 70:763–770 (1992), which is hereby incorporated by reference. One equivalent of 3-hydroxy-2-methyl-4-pyrone and two equivalents of glycine are dissolved in hot distilled water, the pH is adjusted to approximately 9 with 8N sodium hydroxide, and the reaction mixture is heated under reflux for 20 hours. After cooling and decolorizing with charcoal, approximately half of the solvent is removed under vacuum and 6N hydrochloric acid is added to reduce the pH to approximately 3. A yellow solid precipitates which yields the product as off-white crystals after two recrystallizations from water (mp 258°–260° C.).

Method B

This method is adapted from GB Patent No. 2,11 8,176A to Hider et al., which is hereby incorporated by reference. In brief, a 3-hydroxy-4-pyrone is converted to the corresponding 3-benzyloxy-4-pyrone via reaction with benzyl chloride. A methanolic solution of the pyrone is added to an aqueous solution of sodium hydroxide after which benzyl chloride is added and the reaction mixture refluxed for approximately 6 hours. The solvent is evaporated under reduced pressure, water is added, and then the product is extracted into an appropriate organic solvent. After washing, the extract is dried over anhydrous magnesium sulfate and the solvent evaporated to yield the crude 3-benzyloxy derivative which is used in the next step without further purification. To a solution of the 3-benzyloxy compound in an appropriate solvent is added a slight excess of primary amine. The reaction mixture is stirred at room temperature for approximately 6 days after which it is acidified to pH 2 with concentrated hydrochloric acid and evaporated to dryness. The residue is washed with water and extracted into an appropriate organic solvent which is then dried over magnesium sulfate and evaporated to dryness. To the residue is added hydrobromic acid. This reaction mixture is heated on a steam bath for 30 minutes and then recrystallized from water to yield the N-substituted 3-hydroxypyrid-4-one. The product melts sharply and has an NMR spectrum consistent with the desired product. This synthesis is depicted as follows:

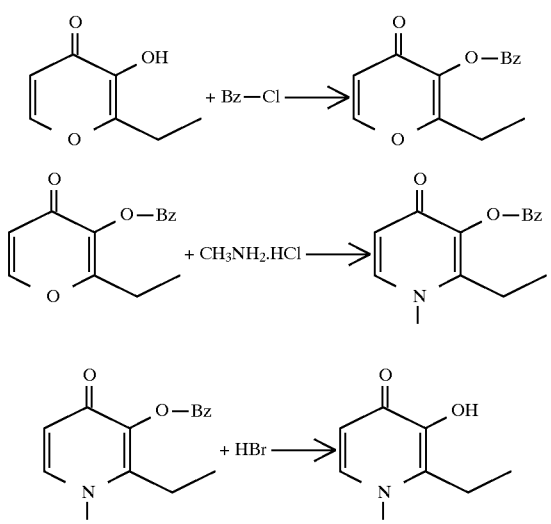

In particular, 2-ethyl-3-hydroxy-4-pyrone (24.7 g) in 225 ml of methanol is added to 25 ml of water containing 7.5 g of sodium hydroxide. To this solution is added benzyl chloride (25.5 g) and the mixture is then refluxed for 6 hours. Upon cooling, the solvent is removed under reduced pressure. The residue is treated with 50 ml of water and then extracted three times with 25-ml aliquots of dichloromethane. The combined extracts are washed twice with 50% (w/v) sodium hydroxide, then twice with 25 ml of water and dried over magnesium sulfate. Evaporation of the solvent yields crude 3-benzyloxy-2-ethyl-4-pyrone. This crude pyrone (24.4 g) and 1.56 g of methylamine hydrochloride are then dissolved in 300 ml of aqueous ethanol (100 ml) containing 2 g of sodium hydroxide. The solution is stirred at room temperature for 6 days, acidified to pH 2 with concentrated hydrochloric acid, and then evaporated to dryness. The residue is washed with water and extracted twice into chloroform (50 ml). The combined extracts are dried over anhydrous magnesium sulfate and evaporated to dryness yielding 3-benzyloxy-2-ethyl-1-methylpyrid-4-one. To 2 g of this pyrid-4-one is added concentrated hydrobromic acid (10 ml). The reaction mixture is heated on a steam bath for 30 minutes, and the product is recrystallized from water to yield 2-ethyl-3-hydroxy-1-methylpyrid-4-one.

Method C

This method is adapted from that of Bartulin et al., *J. Heterocyclic Chem.* 29:1017–1019 (1992), which is hereby incorporated by reference. A 3-benzyloxy-4-pyrone, prepared as in Method B, is added to an ethanolic solution of aqueous ammonia. The reaction mixture is stirred for approximately 3 days, concentrated under reduced pressure, triturated with acetone, and the solid recrystallized from ethanol to yield the corresponding 3-benzyloxypyrid-4-one. To a solution of this pyrid-4-one in aqueous ethanol containing one equivalent of sodium hydroxide was added an equivalent of n-alkyl bromide. The reaction mixture was heated under reflux for 24 hours after which it was cooled, concentrated under reduced pressure, and extracted with an appropriate solvent. After washing, the organic phase with water, it is dried over magnesium sulfate. The product is obtained upon concentration of the solution under reduced pressure. Crude 1-alkyl-3-benzyloxypyrid-4-one in acetic acid containing 40% hydrobromic acid is then heated on a steam bath for 30 minutes. The 1-alkyl-3-hydroxypyrid-4-one precipitates and is subsequently recrystallized from benzene in good yield with a narrow melting point and appropriate NMR spectrum. This is shown in the following synthesis:

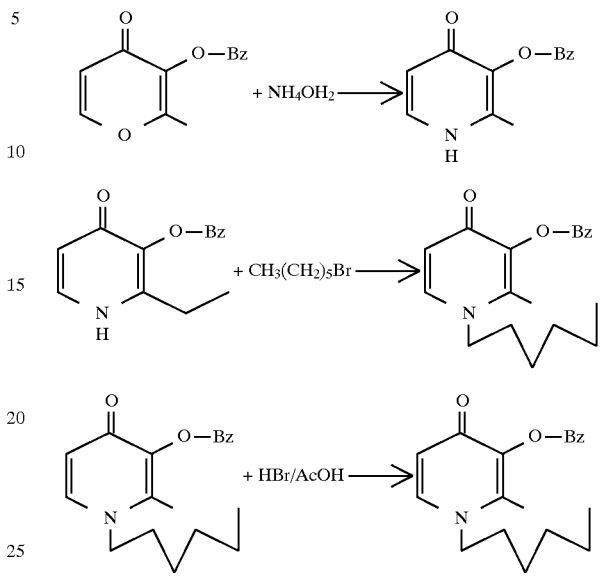

In particular, 3-benzyloxy-2-methyl-4-pyrone was prepared as described in Method B. A solution containing 15.3 g of the pyrone, 160 ml of aqueous ammonia (25%), and 80 ml of ethanol is stirred at room temperature for 3 days. The solvent is removed under reduced pressure and some acetone is added. The solid which precipitates is collected by filtration and recrystallized from ethanol to yield (80%) 3-benzyloxy-2-methylpyrid-4-one with a melting point of 162°–163° C. A solution containing 0.125 moles of the pyrid-4-one, 0.125 moles of n-hexyl bromide, 0.125 moles of sodium hydroxide, 25 ml of water, and 200 ml of ethanol is heated under reflux for 24 hours. After removal of the solvent under vacuum, the residue is extracted with ethyl ether. The etherial solution is washed with water yielding a precipitate which is crystallized from benzene after drying to give 3-benzyloxy-1-hexyl-2-methylpyrid-4-one (95%, mp 46° C.). A solution of this compound in 80 ml of acetic acid containing 40% hydrobromic acid is then heated on a steam bath for 30 minutes. The product is filtered off and crystallized from benzene to yield 1-hexyl-3-hydroxy-2-methylpyrid-4-one in 70% yield.

Compounds of Formula (II)

Compounds of Formula (II) are synthesized by the general procedure outlined in GB Patent No. 1,118,176A to Hider et al., which is hereby included by reference. In brief, 2,3-dihydroxypyridine is mixed with an organic halide in a sealed tube and heated at 140° C. for 24 hours. The tube is then cooled in an acetone/dry ice bath and opened. The excess halide is poured off, and water is added to the dark residue. Sulfur dioxide gas is bubbled through the mixture until the aqueous phase becomes clear. The pH of the reaction mixture is then adjusted to approximately 6 with sodium carbonate, and the resulting solution is extracted with an appropriate solvent after saturation with ammonium sulfate. The organic extracts are dried over anhydrous sodium sulfate and concentrated under reduced pressure to yield a solid which gives the desired N-substituted 3-hydroxypyrid-2-one after crystallization from petroleum ether.

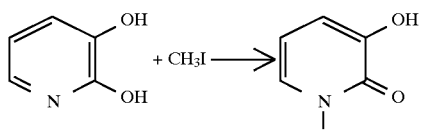

In particular, 5.6 g of 2,3-dihydroxypyridine in 20 ml of methyl iodide are heated in a sealed tube at 140° C. for 24 hours. The tube is cooled in acetone/dry ice, opened, and the excess methyl iodide poured off. Distilled water (10 ml) is added, and the solution is treated with sulfur dioxide until clear. The pH of the reaction mixture is adjusted to 6 with aqueous sodium carbonate (1M) after which the resulting solution is saturated with ammonium sulfate followed by extraction with chloroform until the chloroform layer fails to give a blue color with aqueous ferric chloride. The combined extracts are dried over sodium sulfate after which the solvent is removed under reduced pressure and the residue crystallized from petroleum ether to give 3-hydroxy-1-methylpyrid-2-one.

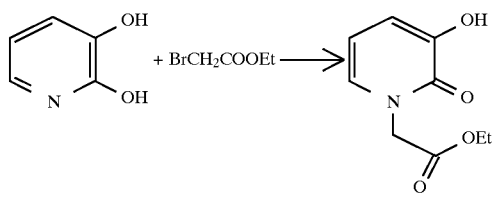

A related compound, 1-ethoxycarbonylmethyl-3-hydroxypyrid-2-one, is prepared by heating a mixture of 2,3-dihydroxypyridine (5 g) and 20 ml of ethylbromoacetate in a sealed tube at 140° C. for 24 hours, as described by GB Patent No. 4,585,780 to Hider et al., which is hereby incorporated by reference. After cooling in solid $CO_2$, the tube is opened, the reaction mixture poured off, and evaporated to dryness under vacuum to yield a yellow solid. Recrystallization from water yields the product as white crystals (5.4 g), MP 141°–151° C.

By applying the warhead strategy, suitable compounds, e.g., of Formulae (I) or (II), can be attached to carriers as defined above, which mimic the substrate motif of the protein hydroxylases. This optimizes the interaction of such compounds with the active site metal ion of these enzymes in order to block intracellular hypusine formation. Carriers can be the physiological substrate motifs in their peptide form or peptidomimetic molecules of these motifs that are biologically stable and cell membrane permeable. Examples are:

1. A peptide carrier of the substrate motif G-m*-x-G-type for inhibition of deoxyhypusyl hydroxylase, to be equipped with an appropriate compound of Formulae (I) or (II), such as 1-carboxymethyl-3-hydroxy-2-methylpyrid-4-one or 1-carboxymethyl-3-hydroxypyrid-2-one, respectively. Peptides of the sequence Ac-Dab(A)-H-G-OH, in which A denotes a radical of the Formulae Ia or IIa

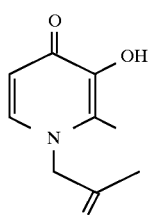

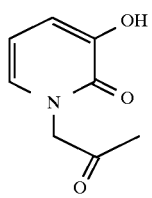

are prepared in analogy to the general procedure for synthesis of catecholpeptides as outlined in U.S. Pat. No. 4,797,471 to Teetz et al., which is hereby incorporated by reference. There, Ac is acetate, Dab is 2,4-diarninobutyric acid, A is a residue constituting a warhead, H is histidine, G is glycine, and OH is hydroxyl. The starting materials are Ac-Dab-H-G-O-Bzl, and the 3-benzyloxy derivative is one of the appropriate hydroxypyridones, all synthesized by conventional methods. The C-terminal substituent '—O-Bzl' is benzyl ether. The peptide and the appropriate 3-benzyloxypyridone derivative are coupled using a carbodiimide protocol, i.e., they are dissolved in dimethylformamide in the presence of 1-hydroxybenzotriazole and N-ethylmorpholine, and allowed to react at room temperature for 18 hours after addition of dicyclohexylcarbodiimide, as described by U.S. Pat. No. 4,797,471 to Teetz et al. The solvent is removed under vacuum, the residue immediately dissolved in methanol, and, after addition of Pd/C, hydrogenolytically cleaved. When the cleavage is complete, as evidenced by thin layer chromatography, the catalyst is removed by filtration, and the filtrate concentrated in vacuo.

2. A peptidomimetic carrier of the substrate motif G-m*-x-G for inhibition of deoxyhypusyl hydroxylase, to be equipped with an appropriate moiety of Formulae (I) or (II), where x indicates the presence of any residue. The β-turn mimetic of Formula III

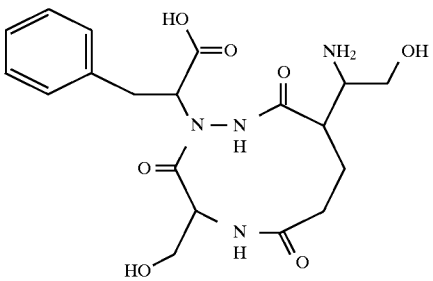

was synthesized according to the method published by Chen et al., Proc. Natl. Acad. Sci. USA 89:5872–5876 (1992), which is hereby incorporated by reference. Briefly, the precursor azetidinone was prepared by a technique analogous to Salzmann et al., J Am. Chem. Soc. 102:6161–63 (1980) and to Williams et al., J. Am. Chem. Soc. 111:1073–83 (1989), which are hereby incorporated by reference. Intermediate reaction steps are: i) mixed anhydride coupling of azetidinone to O-benzyl serine benzyl ester, followed by hydrogenolytic cleavage of the benzyl ester to generate intermediate A; ii) reaction of intermediate A with Z-protected hydrazinophenylalanine, giving intermediate B; iii) using intermediate B, reductive closure, saponification, and hydrogenolytic deprotection of the side chain-protecting groups afforded the product III which was tested to verify its ability to interact as a peptidomimetic with the enzyme. For the purpose of using this compound as a carrier, appropriate warheads, e.g. a moiety of Formulae (I) or (II), can be introduced in the course of building up the ring structure of Formula III.

The compounds of the present invention can be used to treat a number of viral diseases caused by viruses that require a specific regulator (i.e. Rev or a functional equivalent) to express viral structural genes and to propagate efficiently. Such viruses include, but are not limited to, the lentiviruses pathogenic for humans and animals, in particular the human, bovine, feline, and simian immunodeficiency viruses, the equine infectious anemia virus, the caprine arthritis-encephalitis virus, and the visna virus.

These compounds can be administered topically or systemically. More particularly, such administration can be orally; parenterally, i.e. by subcutaneous, intravascular, or intramuscular injection; intraperitoneally; intrathecally; or by topical application, e.g. to skin or eyes, or by application to the mucous membranes of the nose, throat, bronchial tree, or rectum, etc. They may be administered alone or with suitable pharmaceutical carriers, and can be in solid or liquid form such as tablets, capsules, powders, solutions, suspensions, or emulsions. The dosage of the active compound depends on the species of warm-blooded animal, the body weight, age, and mode of administration.

The pharmaceutical products of the present invention are prepared by dissolving, mixing, granulating, or tablet-coating processes which are known per se.

For oral administration, the active compounds or their physiologically tolerated derivatives such as salts, esters, or amides, are mixed with the additives customary for this purpose, such as vehicles, stabilizers, or inert diluents, and are converted by customary methods into a suitable form for administration, such as tablets, coated tablets, hard or soft gelatin capsules, aqueous, alcoholic, or oily suspensions, or aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils, such as sunflower oil or fish-liver oil. Preparations can be effected both as dry and as wet granules.

For parenteral administration (subcutaneous, intravascular, or intramuscular injection), the active compounds or their physiologically tolerated derivatives such as salts, esters, or amides, are converted into a solution, suspension, or emulsion, if desired, with the substances customary and suitable for this purpose, such as solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as propylene glycol or polyethylene glycol, are preferred liquid carriers, particularly for injectable solutions.

For use as aerosols, the active compounds or their physiologically tolerated derivatives such as salts, esters, or amides, may be dissolved or suspended in a physiologically acceptable liquid and packaged in a pressurized aerosol container together with suitable propellants, for example, hydrocarbon propellants like propane, butane, or isobutane with conventional adjuvants. The agents which block intracellular hypusine formation, in accordance with the present invention, may also be administered from a non-pressurized container such as a nebulizer or atomizer.

For topical administration to external or internal body surfaces, e.g., in the form of creams, gels, or drops, etc., the active compounds or their physiologically tolerated derivatives such as, salts, esters, or amides, are prepared and applied as solutions, suspensions, or emulsions in a physiologically acceptable diluent with or without a pharmaceutical carrier.

The present invention is illustrated by the following examples.

EXAMPLES

EXAMPLE I

Inhibition of deoxyhypusyl hydroxylase

The suppressive effect of hypusine inhibitors was studied at the level of the eIF-5A-hydroxylating enzyme deoxyhypusyl hydroxylase ("DOHH") by using either a cell-free enzyme assay or by determining the deoxyhypusine-to-hypusine conversion in cultured human cells. The cell-free enzyme assay was performed to test a pilot peptidomimetic which can be equipped with hydroxypyridone warheads. The cell culture studies were performed to establish the inherent inhibitory potency of such hydroxypyridones.

A. Cell-free system

Methods.

DOHH Assay. Enzyme activity was purified and determined, as described by Abbruzzese et al., *J Biol Chem* 261:3085–9 (1986), which is hereby incorporated by reference. Briefly, the enzyme is offered as labeled deoxyhypusine-containing eIF-5A precursor, and, following standard incubation conditions, the conversion into hypusine residues is measured by chromatographic amino acid separation of the hydrolyzed proteins. It has been previously established that hydroxypyridones, e.g. mimosine, act as hypusine inhibitors in this cell-free system [Hanauske-Abel et al., *Biochim. Biophys. Acta,* 1221, 115–124 (1994), which is hereby incorporated by reference].

Results.

Figure 4A:
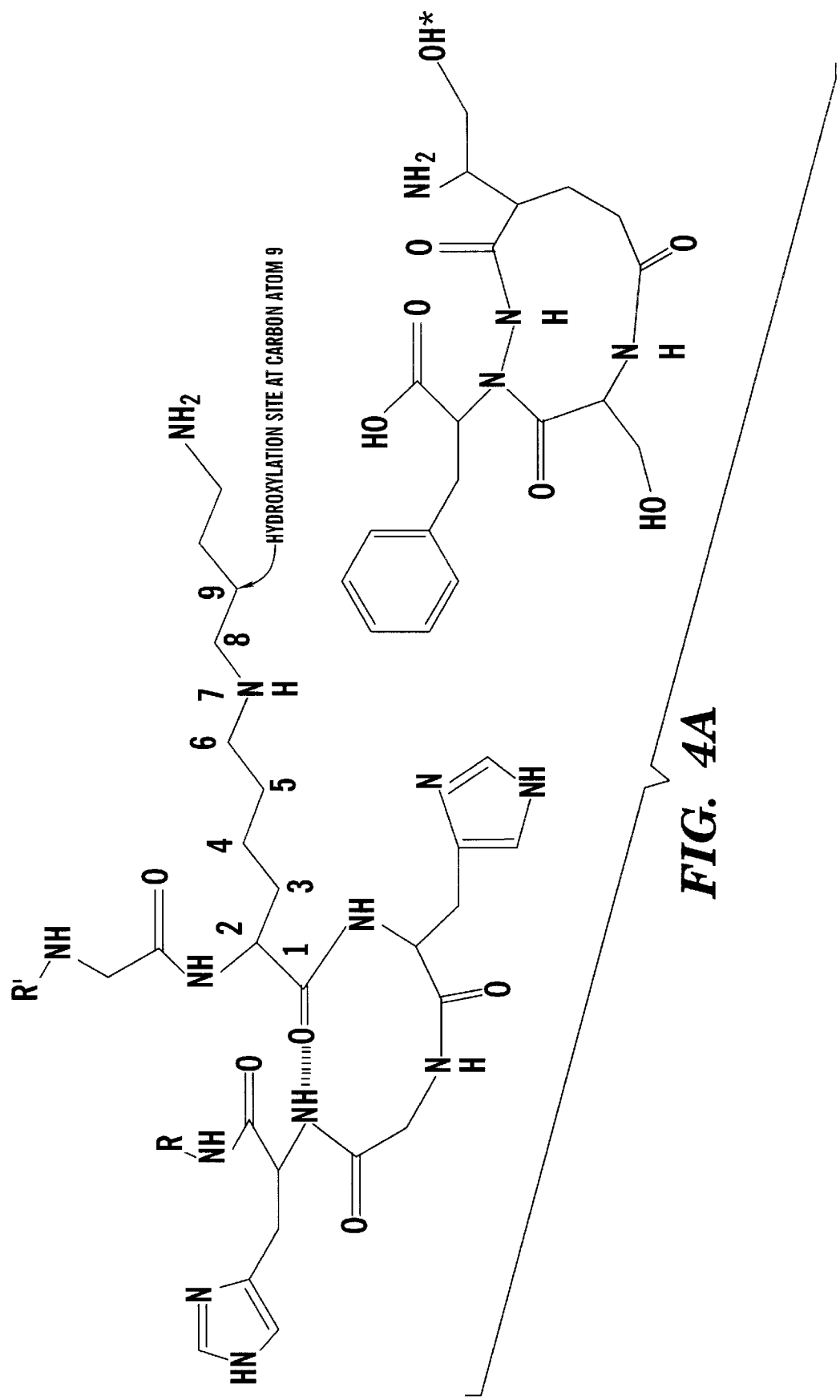
FIG. 4A shows the design of a non-peptide analog termed mimetic III of the DOHH substrate motif, while FIG. 4B displays the results of the testing of this peptidomimetic using purified DOHH. The graph gives the chromatographic profile of metabolically labeled hypusine/deoxyhypusine obtained after incubation of the purified rat enzyme with unhydroxylated eIF-5A in the absence (open squares) and presence (closed squares) of mimetic III. In the presence of mimetic III, the DOHH-mediated conversion of deoxyhypusine to hypusine was clearly reduced. Peptides of appropriate structure or peptidomimetics like mimetic III can serve as "carriers" for a reactive moiety termed "warhead" that, by virtue of its attachment to the carrier, becomes precisely oriented to interact optimally with the active site metal ion of DOHH. In the case of mimetic III, such a warhead moiety can be attached at the site indicated by the asterisk in FIG. 4A.
Figure 4B:
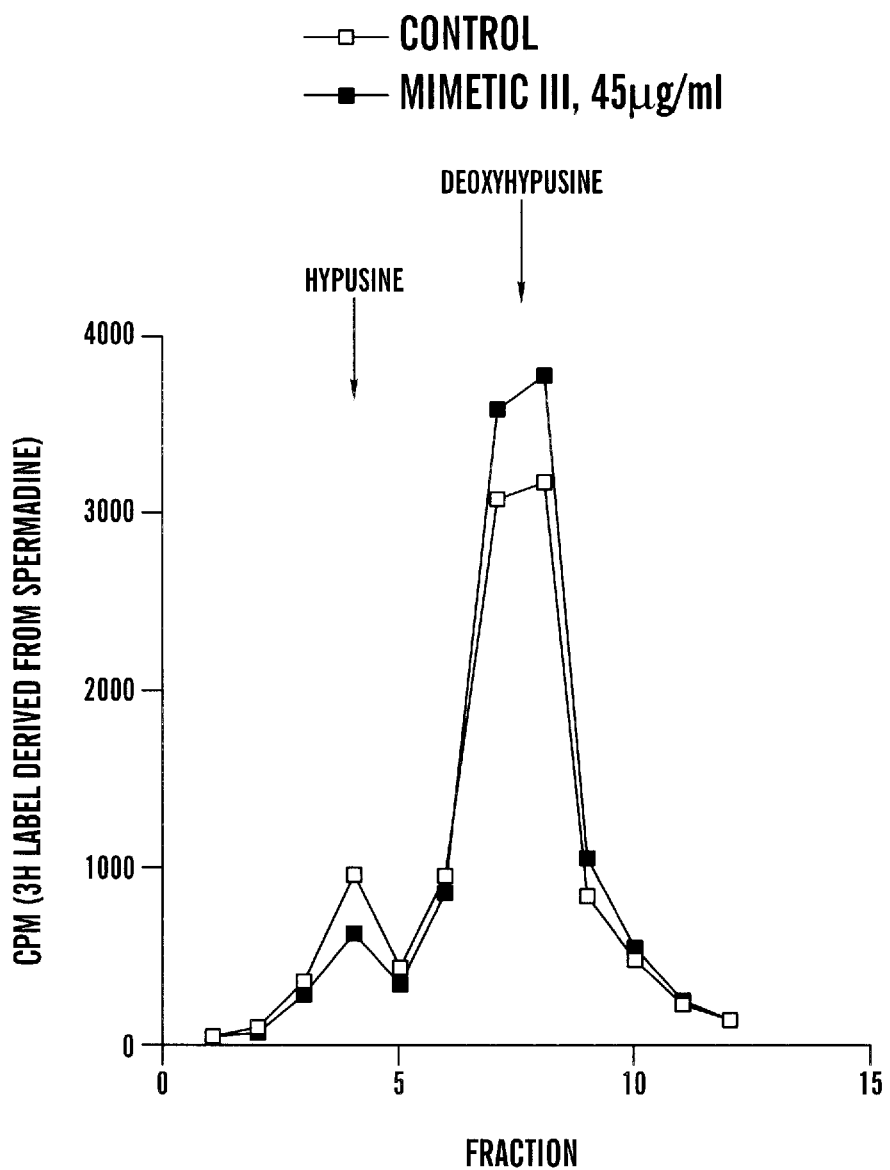

FIG. 4A shows that mimetic of Formula III (i.e. mimetic III) was designed as a covalently stabilized analogue of the B-turn conformation known to be optimal for -G-x-y-G-motifs when occurring within the structure of the native protein substrates of deoxyhypusyl hydroxylase and the collagen hydroxylases [for example, Atreya et al., *J. Biol. Chem.* 266, 2852–2858 (1991), which is hereby incorporated by reference]. The mimetic of Formula III also serves as a potential carrier for inhibitory moieties which, designed to be oriented towards the hydroxylation site, become optimally positioned for interaction with the catalytically active metal ion of DOHH [Abbruzzese, Hanauske-Abel et al., *Biochim. Biophys. Acta* 1077, 159–166 (1991), which is hereby incorporated by reference]. In the case of peptidomimetic molecules, such a reactive moiety can be attached to an appropriately oriented functional group, as indicated by the asterisk in FIG. 4A. The effect of the pilot compound, the mimetic of Formula III, on the hydroxylation of the -G-x-y-G-containing segment of the eIF-5A precursor was studied using unhydroxylated eIF-5A precursor and purified deoxyhypusyl hydroxylase. As shown in FIG. 4B, the deoxyhypusine-to-hypusine conversion was suppressed by the presence of the mimetic of Formula III, i.e., hydroxylation was inhibited while the unhydroxylated precursor remained unutilized.

B. Cellular system
Methods.

DOHH Assay. The intracellular conversion of peptide-bound deoxyhypusine to peptidyl hypusine was determined after preincubation of human T lymphocyte-derived cells (i.e. ACH-2) [Clouse et al., *J. Immunol.* 142, 431–438 (1989), which is hereby incorporated by reference] with the hypusine inhibitors mimosine and HK-1 for 60 minutes, followed by labeling for 21 hours with $^3$H-spermidine (3.75 $\mu$Ci/ml) in wells containing $3 \times 10^6$ cells suspended in 8 ml of serum-supplemented and antibiotic-containing RPMI 1640 medium. Cells were then split into two groups, one of them being harvested immediately to assess degree of DOHH inhibition, and the other harvested after transfer of the cells into inhibitor-free medium for 2 hours to measure resumption of DOHH activity. Harvesting consisted in precipitation of washed cells with 10% TCA containing 1 mM each of putrescine, spermidine, and spermine. Cellular proteins from each sample were then hydrolyzed in 6N HCl at 110° C. for 16 hours. The hydrolysate was analyzed for labeled amino acids on an amino acid analyzer by published methods [Park et al., *J. Biol. Chem.*, 257, 7217–7222 (1982), which is hereby incorporated by reference]. The retention times of hypusine and deoxyhypusine were determined from standards. Similar studies were performed in human B-cells and human smooth muscle cells.

Results.

The results presented in Table 1, obtained in human B-cells and human smooth muscle cells, indicate that L-mimosine and other representative hydroxypyridones efficiently inhibit deoxyhypusyl hydroxylase activity, i.e. hypusine formation. The concentration required for half-maximal inhibition ($ID_{50}$) of the cellular enzyme activity is identified for each compound.

It has been shown before that hydroxypyridones, such as mimosine, inhibit purified and cellular deoxyhypusyl hydroxylase, i.e. the formation of eIF-5A. This effect displayed the same reversibility, the same dose- and time-dependency, and the same structure-activity relationship as the parallel inhibition of cellular proliferation [Hanauske-Abel et al., *Biochim. Biophys. Acta* 1221, 115–124 (1994), which is hereby incorporated by reference]. It was proposed that a causal link exists between hypusine inhibition and proliferative arrest, i.e. that the eIF-5A-dependent loading of specific cellular mRNAs onto polysomes is required for effective translation of specific proteins which, in turn, enable and initiate replication of cellular DNA. Indeed, a small number of cellular mRNAs was subsequently detected which disappear from and reappear at polysomes in concert with inhibition and disinhibition, respectively, of hypusine formation [Hanauske-Abel et al., *FEBS Lett.* 366, 92–98 (1995), which is hereby incorporated by reference]. A virus which parasitizes this pathway of eIF-5A-directed polysomal translation in the interest of achieving a replicative advantage for itself, would display hypusine-dependent polysomal localization of viral MRNA, hypusine-dependent translation of viral protein, and hypusine-dependent production of infectious viral particles. It was reported that the Rev protein of the human inununodeficiency virus type 1 (HIV-1) physically interacts with and recruits eIF-5A for its biological functions [Ruhl et al., *J. Cell. Biol.* 123, 1309–1320 (1993), which is hereby incorporated by reference]. Accordingly, applicants hypothesized that HIV-1- infected cells should display the aforementioned effects upon exposure to hypusine inhibitors. Moreover, the lack of bioactive eIF-5A due to inhibition of hypusine formation would constitute the pharmacologic equivalent of mutational Rev deficiencies which are known to alter profoundly the splic-

TABLE 1

| | R1 | R2 | Deoxyhypusyl hydroxylase ID50 (cellular) |
|---|---|---|---|
| L-Mimosine | —CH$_2$CH(NH$_2$)COOH | H | 65 |
| HK-1, CP20, L1, DMHP, Deferiprone | —CH$_3$ | —CH$_3$ | 90 |
| HK-2, CP94 | —CH$_2$CH$_3$ | —CH$_2$CH$_3$ | 50 |
| HK-15, CP51 | —(CH$_2$)$_2$OCH$_3$ | —CH$_3$ | 60 |
| HK-16 | —CH$_2$CH=CH$_2$ | —CH$_3$ | 50 |
| HK-26 | —CH$_2$CH$_3$ | —CH$_3$ | 58 |
| HK-27 | —(CH$_2$)$_2$CH$_3$ | —CH$_3$ | 50 |

Figure 5:
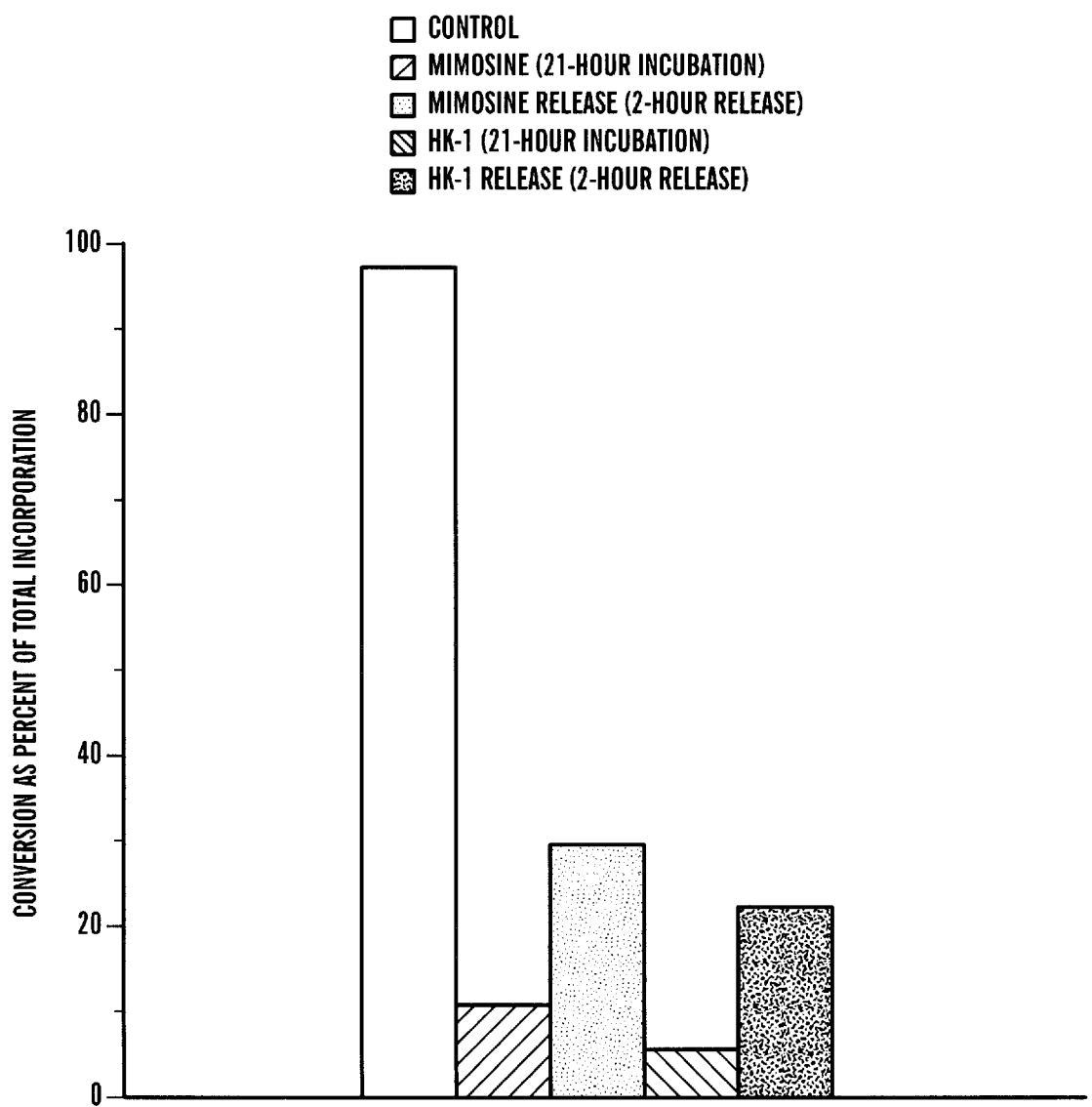
FIG. 5 shows the effect of mimosine and HK-1, each applied for 22 hours at a concentration of 200 $\mu$M, on the deoxyhypusine-to-hypusine conversion mediated by the DOHH activity in human T-lymphocyte cell line (ACH-2). Both compounds reduced the conversion, which was close to 100% in untreated cells (open column), to 10% or less (darkly hatched columns). Within 2 hours of inhibitor removal and re-incubation in fresh medium, conversion resumed and almost tripled (lightly hatched columns).

In FIG. 5, the suppressive effect of 200 $\mu$M mimosine and HK-1 in the human T-cell line ACH-2 is shown. At this concentration, the deoxyhypusine-to-hypusine conversion, which exceeds 95% in control cells, drops to less than 10%, but recovers readily and triples within the first 2 hours of inhibitor removal.

EXAMPLE II

Selective reduction of viral mRNA localization to polysomes, and induction of defective spicing of viral RNA which mimics splicing defects due to mutational Rev deficiencies.

ing pattern of HIV-1 mRNAs, affecting the ability of infected cells to generate intron-containing about 9- and about 4-kb transcripts, i.e., the RNAs constituting the infectious viral genome and needed for the biosynthesis of the viral structural proteins [see for instance Malim et al., *Mol.Cell. Biol.* 13, 6180–6189 (1993), which is hereby incorporated by reference].

A. Polysomal localization
Methods.

The human T-cell line ACH-2, a subclone of the A3.01 variant of the CEM T-cell line, contains in its genetic material a single copy of the HIV-1 genome as an integrated provirus and exhibits minimal constitutive expression of HIV-1 [Clouse et al., *J. Immunol.* 142, 431–438 (1989), which is hereby incorporated by reference]. However, vigorous HIV-1 production by ACH-2 cells is induced by addition of the phorbol ester PMA [Pomerantz et al., *Cell* 61, 1271–1276 (1990) and Michael et al., *J. Virol* 65, 1291–1303 (1991), which are hereby incorporated by reference]. This system was selected for these experiments. Logarithmically growing ACH-2 cells, suspended at a concentration of $3\times10^5$/ml, were incubated with the hypusine inhibitors mimosine and HK-1 at a final concentration of 200 $\mu$M. After 8 hours, viral replication was activated by addition of PMA to these cells and to untreated controls (100 ng/ml final PMA concentration). Following a further 13 hours of incubation, all samples were harvested and the polysomal and non-polysomal mRNA of each sample fractionated by sucrose gradient centrifugation; 0.5 ml-fractions were collected as described in Hanauske-Abel et al., *FEBS Lett.* 366, 92–98 (1995), which is hereby incorporated by reference. Each fraction was then extracted with phenol-chloroform (1:1), and the RNA was precipitated with two volumes of ethanol. An aliquot of each fraction was analyzed by slot blotting, using the pXC-1 genomic ribosomal DNA probe from rat containing the 18S rRNA coding sequence [Rimarachin, Szabo et al., *In Vitro* 28A, 705–707 (1992), which is hereby incorporated by reference], to determine the location within the gradient of 18S rRNA, i.e., the distribution of polysomes vs. monosomes. The mRNA of each fraction was then used to generate cDNA by reverse transcription employing a standard protocol. The cDNA of each fraction was analyzed by semi-quantitative PCR methodology employing two sets of oligonucleotide primer pairs, one specific for viral Rev-dependent transcripts containing the gag open reading frame of the HIV-1 polyprotein p55 {SK38: 5'-ATAATCCACCTATCCCAGTAGGA-3' (SEQ. ID. No. 1); and SK39: 5'-TTTGGTCCTTGTCTTATGTCCAGAATG-3' (SEQ. ID. NO. 2)} and the other one specific for the cellular transcript encoding the 'household' protein D-glyceraldehyde 3-phosphate dehydrogenase ("GAPDH") {Primer A: 5'-CAAAGTTGTCATGGATGACC-3' (SEQ. ID. NO. 3); and Primer B: 5'-CCATGGAGAAGGCTGGGG-3' (SEQ. ID. NO. 4)} [Ben-Yehuda, Szabo et al., *Proc. Natl. Acad. Sci. USA* 91, 11988–11992 (1994), which is hereby incorporated by reference]. Fractions were then loaded side by side onto 6% non-denaturing polyacrylamide gels in the sequence of their elution from the original sucrose gradient. Following electrophoresis, the radio-labeled PCR products were visualized by autoradiography according to routine techniques, and the band intensities quantified by densitometric analysis and expressed relative to total product per gradient.

Results.

Figure 6:
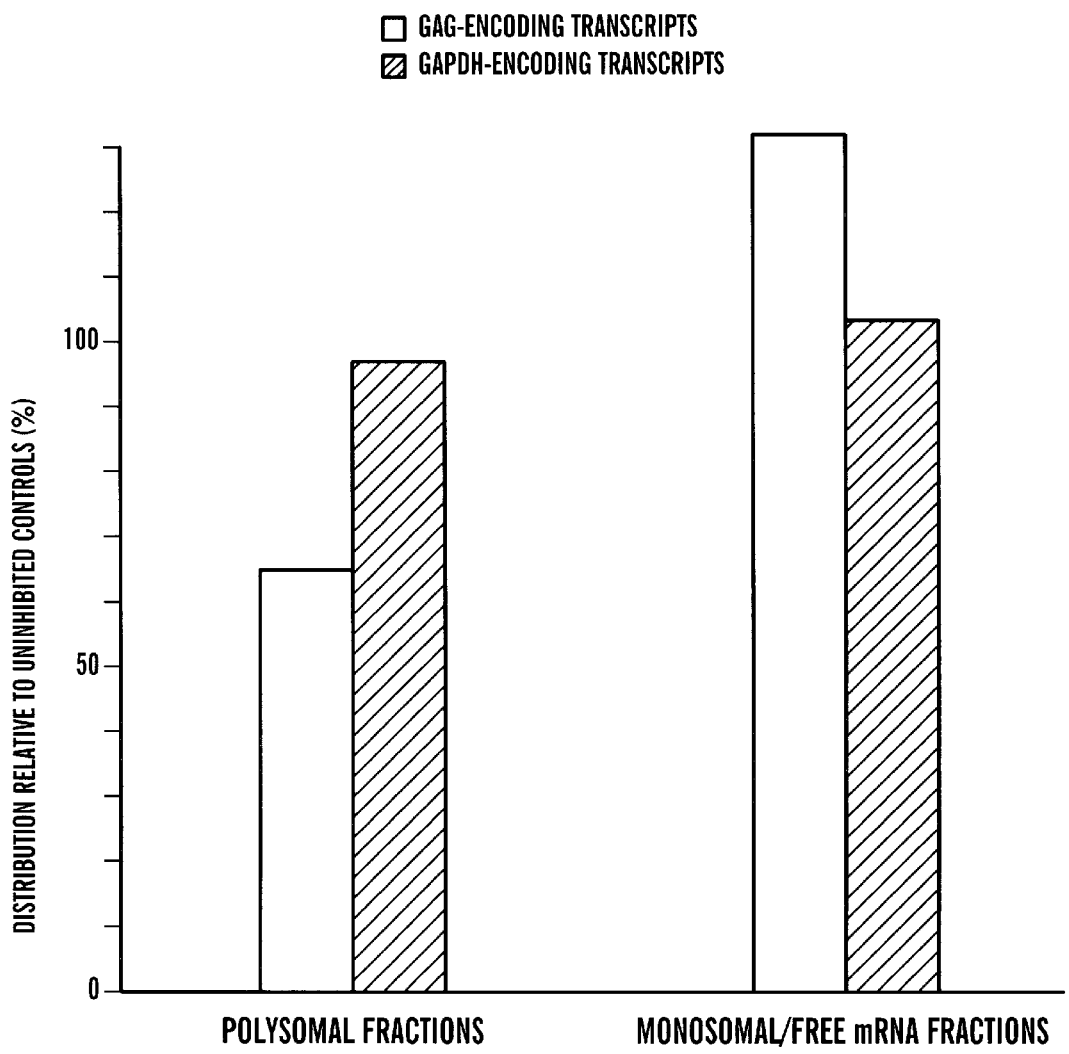
FIG. 6 shows, for the example of incubation with mimosine, the polysomal (columns left) versus non-polysomal (columns right) distribution of two mRNA species obtained from human ACH-2 cells productively infected with HIV-1, one species of viral and the other one of host cell origin, i.e. transcripts encoding, respectively, either the viral Gag protein (dark columns) or the cellular "household" protein D-glyceraldehyde 3-phosphate dehydrogenase (GAPDH; light columns). Upon DOHH-inhibiting incubation with minosine, the viral MRNA species was shifted away from the polysomal protein producing machinery into the pool of monosomal/free MRNA which is biosynthetically inactive. Consequently, hypusine inhibition/eIF-5A failure affected polysomal loading of viral mRNA, but in the same host cells did not affect the polysomal loading of cellular MRNA.

FIG. 6 shows, relative to controls, the effect of the hypusine inhibitor mimosine on the polysomal localization of transcripts encoding the viral protein Gag and the cellular protein GAPDH. Whereas mimosine has only a marginal effect on the distribution of GAPDH mRNA, the compound redirects a significant portion of the Rev-dependent Gag mRNAs into the non-polysomal fractions and thus diverts them away from the protein producing machinery of the cell; the association of mRNA with polysomes, and not just monosomes, is generally accepted as indicating the translational efficacy of that mRNA [see, for instance, Lewin, *Genes V*, Oxford University Press, p.167–171 (1994), which is hereby incorporated by reference]. Similar results were obtained with HK-1 (data not shown), and, consequently, one may reasonably anticipate hypusine inhibitors to reduce selectively biosynthesis of the Gag polyprotein precursor of HIV-1. A relocation of Rev-dependent transcripts away from the polysomes, similar to the one caused by hypusine inhibitors, is also documented to occur in mutationally induced Rev-deficiencies [see, for example, Arrigo et al., *Genes Dev.* 5, 808–819 (1991), which is hereby incorporated by reference].

B. Splicing analysis

Methods.

ACH-2 cells were incubated with hypusine inhibitors (mimosine, HK-1) and induced with PMA as outlined in Example II A. From control cells, from cells induced with PMA, and from PMA-induced cells treated with 200 $\mu$M mimosine/HK-1, in each case aliqouts of $1.2\times10^7$ cells, the total cellular RNA was isolated by the guanidinium isothiocyanate-cesium chloride method [Chirgwin et al., *Biochemistry* 18, 5294–5299 (1979), which is hereby incorporated by reference]. Equal quantities of RNA from each cell sample were electrophoresed on a 1% agarose-formaldehyde gel, transferred to nitrocellulose, and hybridized with randomly primed, $^{32}$P-dCTP-labeled genomic HIV-1 probe pBH10 [Ratner et al., *Nature* 313, 277–284 (1985), which is hereby incorporated by reference]. Following hybridization, the blots were washed extensively, dried, and autoradiographed. These are standard procedural steps for RNA (Northern) blot hybridization.

Results.

Figure 7:
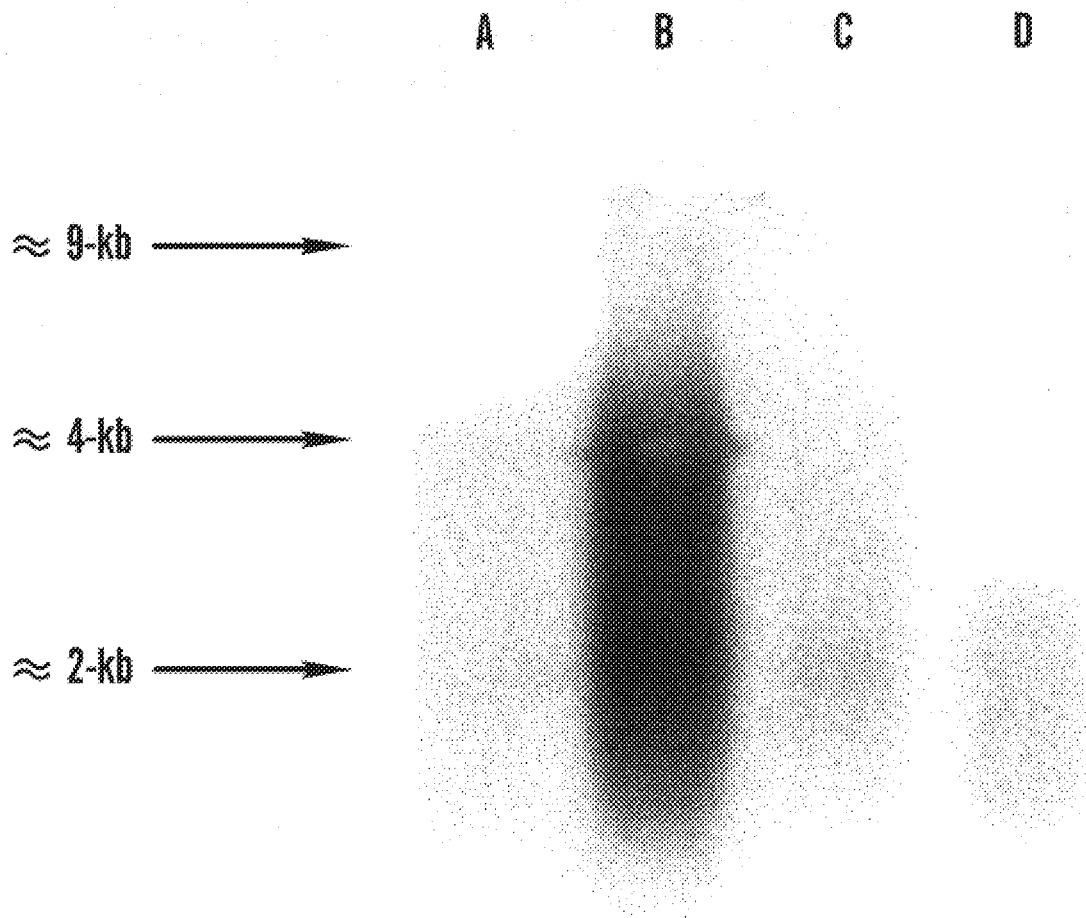
FIG. 7 shows, for the example of incubation with mimosine and HK-1, the effect of pharmacologically induced Rev deficiency due to hypusine inhibition/eIF-5A failure, on the splicing pattern of HIV-1 in a human T-lymphocyte line (ACH-2). At about 9-kb is the position of unspliced viral MRNA species representing the infectious viral genome and encoding key structural proteins for core and capsid. At about 4-kb is the position of incompletely spliced viral MRNA species encoding structural and regulatory proteins. At about 2-kb is the position of completely spliced viral MRNA species encoding regulatory proteins, such as Rev. Lane A is for the low level expression of HIV-1 RNA in the latently infected ACH-2 cells; note the apparent lack of the 9-kb species. Lane B is for the high level expression of HIV-1 RNA after induction with PMA; note the presence of the 9-kb species. Lane C is for the after induction with PMA as in Lane B, but in the presence of mimosine; note the apparent lack of the 9-kb species. Lane D is for the after induction with PMA as in Lane B, but in the presence of HK-1; note the apparent lack of 9-kb and 4-kb species.

FIG. 7 confirms that quiescent ACH-2 cells make only very small quantities of genomic, about 9-kb HIV-1 RNA, and, preferentially, produce singly or multiply spliced viral transcripts of about 4- and about 2-kb, respectively (lane A). After stimulation with PMA, a marked rise (>10 fold) in all viral transcripts occurred (lane B), and the about 9-kb full length viral RNA species became detectable [Pomerantz et al., *Cell* 61, 1271–1276 (1990), which is hereby incorporated by reference]. Significantly, each hypusine inhibitor not only prevented the PMA-induced increase in the level of total HIV-1 RNA (lanes C and D), but also markedly affected its composition. In particular, the formation of genomic and singly spliced viral RNA was suppressed. This is exactly the pattern previously described in studies of mutational Rev deficiencies such as studied by Malim et al., *Mol. Cell. Biol.* 13, 6180–6189 (1993), which is hereby incorporated by reference. Based on these findings, the biosynthesis of infectious particles and of proteins encoded by the about 9- and about 4-kb viral MRNA species appear to be suppressed by hypusine inhibitors.

EXAMPLE III

Selective inhibition of viral protein biosynthesis and of viral replication, and induction of apoptosis in virally-infected cells.

Based on the data presented in Examples I and II, it was investigated whether hypusine inhibitors suppress viral protein production and viral replication, whether such effects would be selective, and the manner in which virally-infected, human T lymphocyte-derived cells respond to inhibition of eIF-5A formation.

A. Selective inhibition of viral protein biosynthesis and viral replication

Methods.

1. Dose-dependency of antiviral effect. Cells of the human T lymphocyte line H9, chronically and productively infected with the Lai (IIIb) strain of HIV-1, were harvested during logarithmic proliferation, extensively washed to remove viral antigens and infectious particles, and re-suspended in serum-supplemented and antibiotic-containing RPMI 1640 medium at a density of $2\times10^5$ cells/ml. After incubation with increasing concentrations of mimosine or HK-1 for 48 hours, the cells were harvested, lysed, and used to determine the intracellular amount of the p24 antigen derived from the p55 Gag polyprotein, using a commercially available, p24-specific ELISA method (Coulter, Hialeah, Fla.); the same method was also used to quantify the extracellular level of p24 antigen that had accumulated in the supernatant during incubation with the hypusine inhibitors. In addition, titration assays were performed using CEM target cells to measure the infectivity of virus produced in the absence and presence of the hypusine inhibitors using the procedure of Prince et al., *Proc. Natl. Acad. Sci. USA* 85, 6944–6948 (1988), which is hereby incorporated by reference. The half-maximal tissue culture infectious doses ($TCID_{50}$) of HIV-1 per ml of test sample were calculated by the Spearman-Karber method.

2. Selectivity of antiviral effect. ACH-2 cells were incubated with hypusine inhibitors (mimosine, HK-1) and induced with PMA as outlined in Example II A. The supernatants from aliquots ($1.5 \times 10^6$ cells) of control cells, of cells induced with PMA, and of PMA-induced cells treated with 200 μM mimosine/HK-1 were used to co-determine the levels of viral p24 antigen and cellular protein TNF-α, using commercially available ELISA methods (Coulter, Hialeah, Fla. and Genzyme Diagnostics, Cambridge, Mass., respectively).

3. Ultrastructural investigation of antiviral effect. ACH-2 cells were incubated with hypusine inhibitors (mimosine, HK-1) and induced with PMA as outlined in Example II A. Harvesting, fixation of cells, and electron microscopy were performed according to established techniques [Michael et al., *J. Virol* 65, 1291–1303 (1991), which is hereby incorporated by reference].

Results.

Figure 8A:
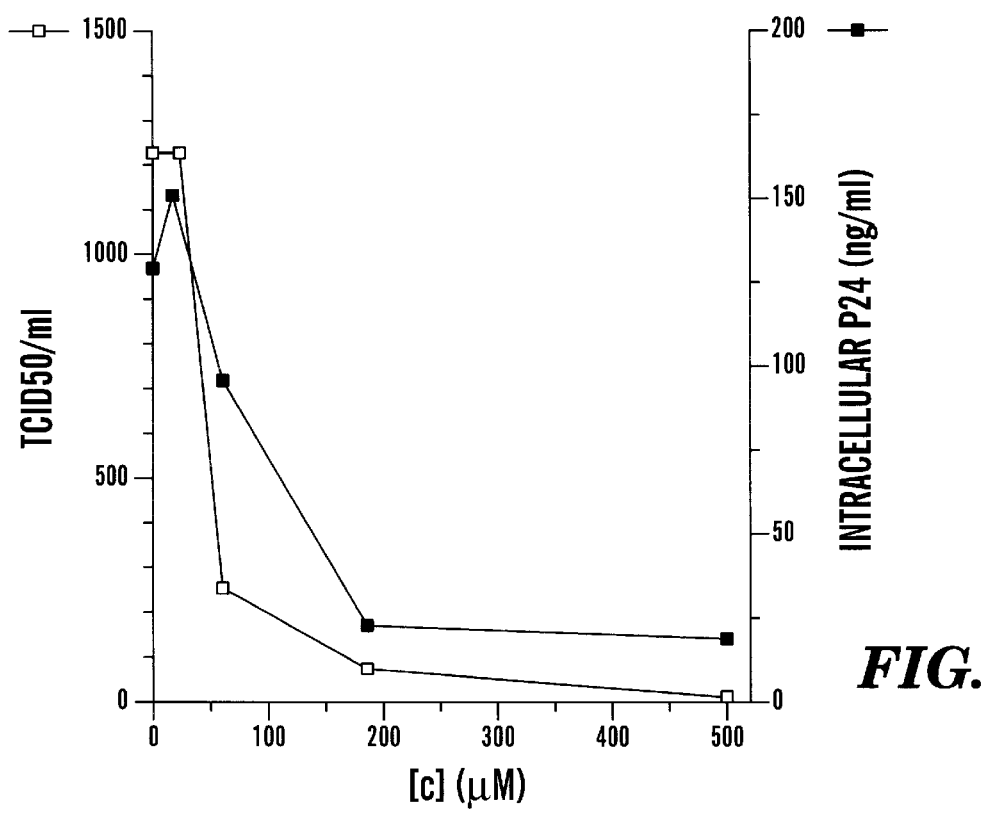
FIGS. 8A and B show, in the chronically and productively infected human T-cell line H9, the dose-dependently suppressive effect of mimosine on the production of infectious HIV-1 particles in conjuction with the inhibitory effect on the intracellular (FIG. 8A) and extracellular (FIG. 8B) levels of the p24 antigen, which is derived from the viral Gag protein.
Figure 8B:
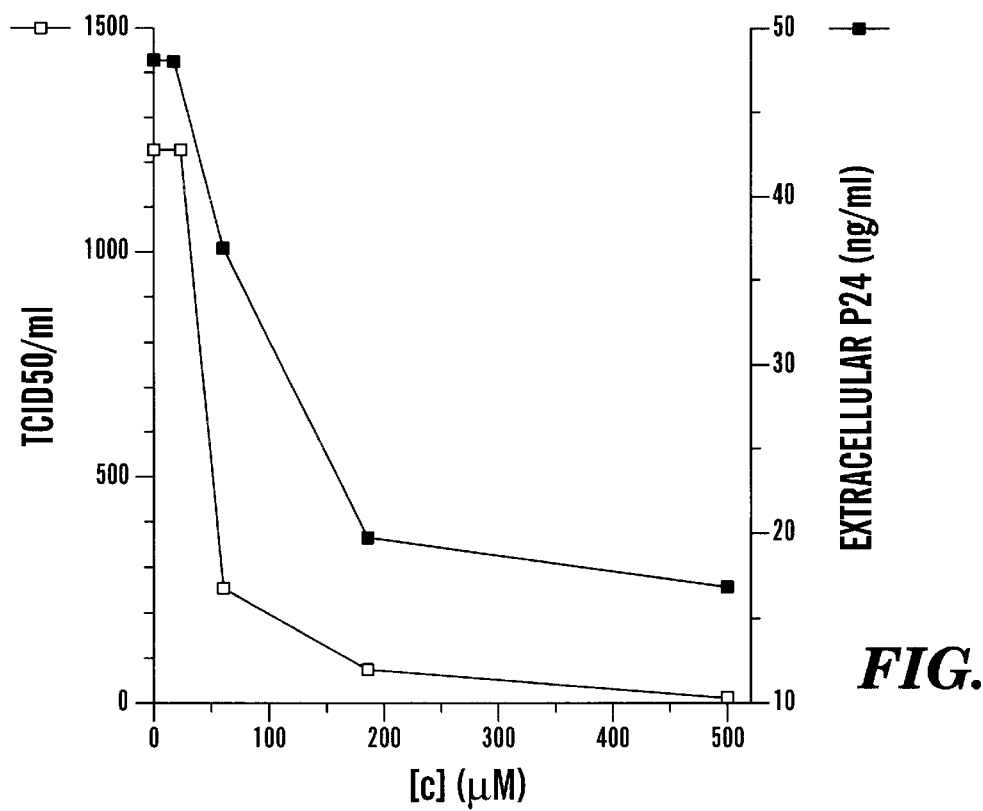
Figure 9A:
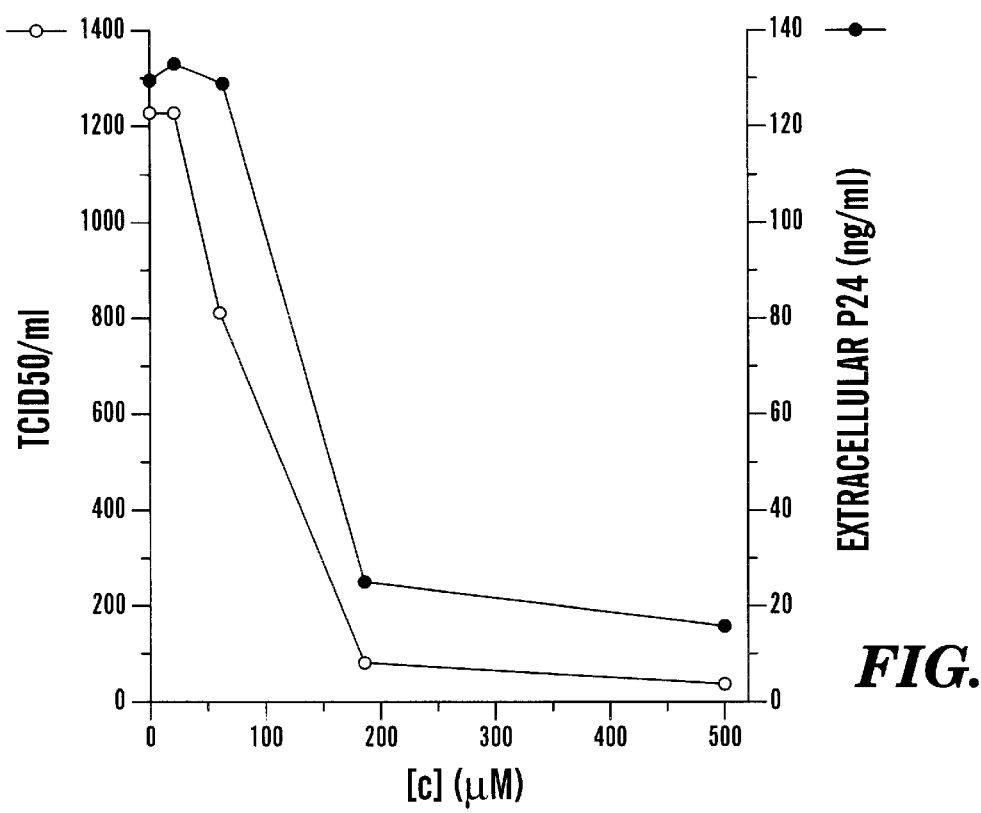
FIGS. 9A and B show, in the chronically and productively infected human T-cell line H9, the dose-dependently suppressive effect of HK-1 on the production of infectious HIV-1 particles in conjunction with the inhibitory effect on the extracellular (FIG. 9A) and intracellular (FIG. 9B) levels of the p24 antigen, which is derived from the viral Gag protein.
Figure 9B:
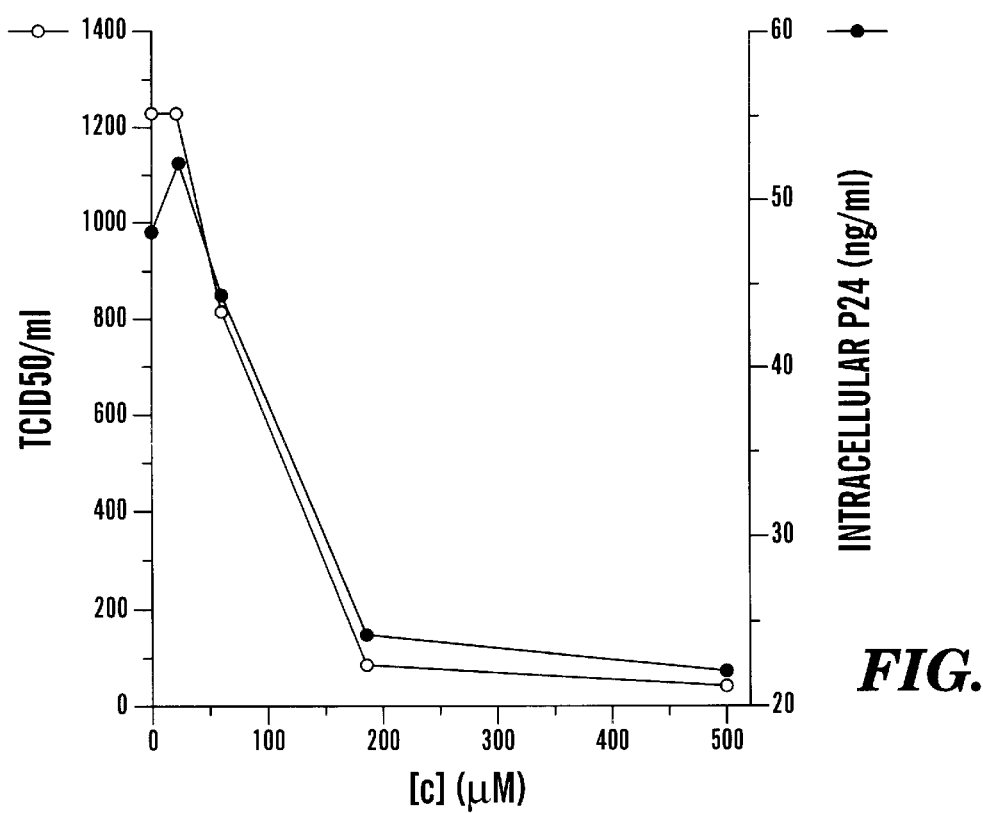
Figure 10:
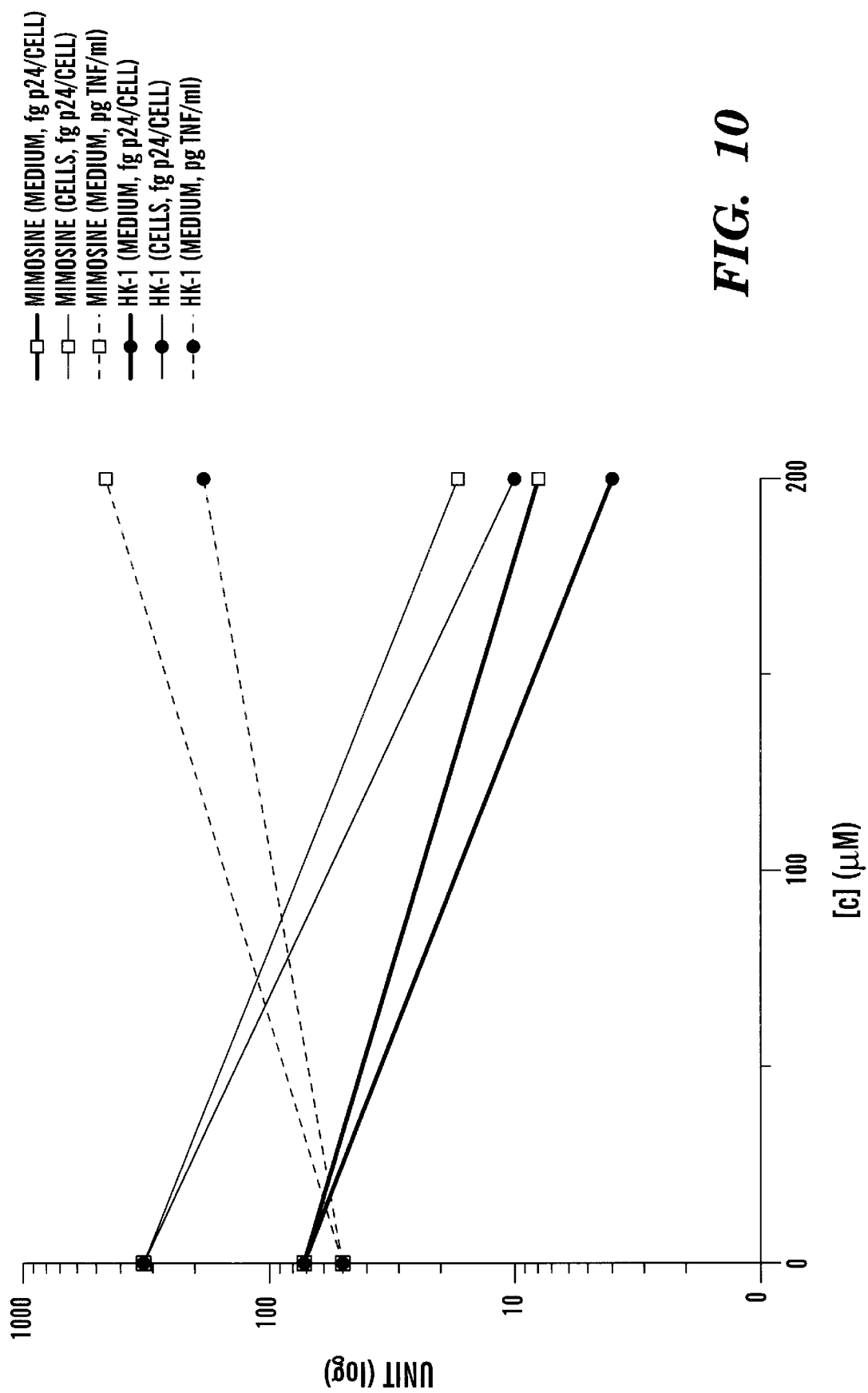
FIG. 10 shows, in PMA-induced and mimosine/HK-1-treated ACH-2 cells, the suppressive effect of the hypusine inhibitors on the levels of the viral p24 antigen in cells (light lines) and supernatant (heavy lines), and the absence of such a suppressive effect on biosynthesis and secretion of a representative cellular protein, TNF-α (dotted lines). Open squares, mimosine; closed circles, HK-1.
Figure 11A:
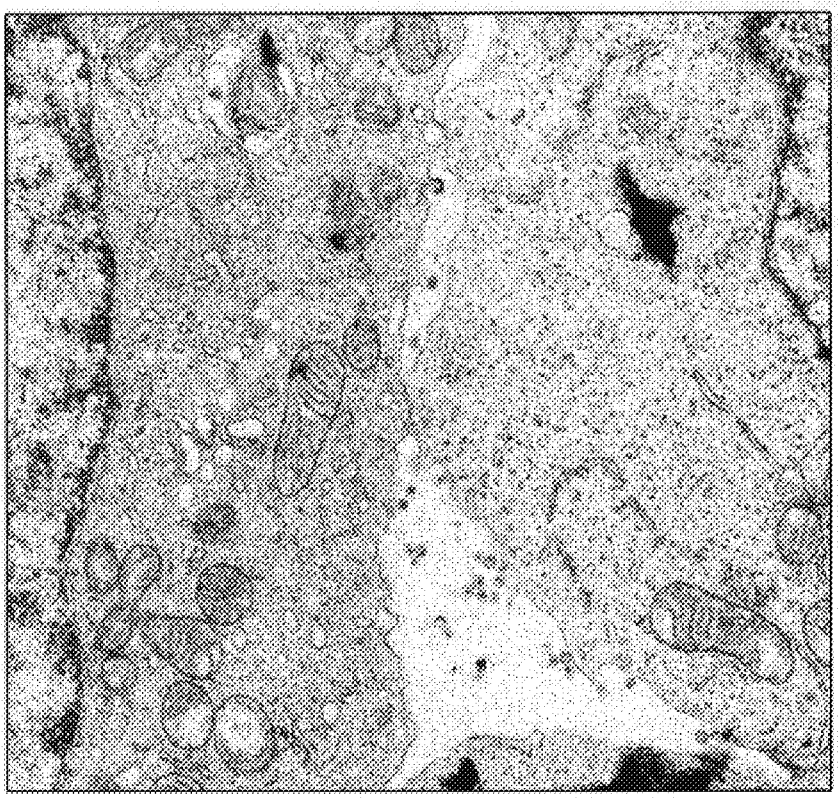
FIGS. 11A and B show, representative ultrastructural findings observed in PMA-induced/untreated (FIG. 11A) and PMA-induced/mimosine-treated (FIG. 11B) ACH-2 cells immediately at the end of the 18-hour incubation period.
Figure 11B:
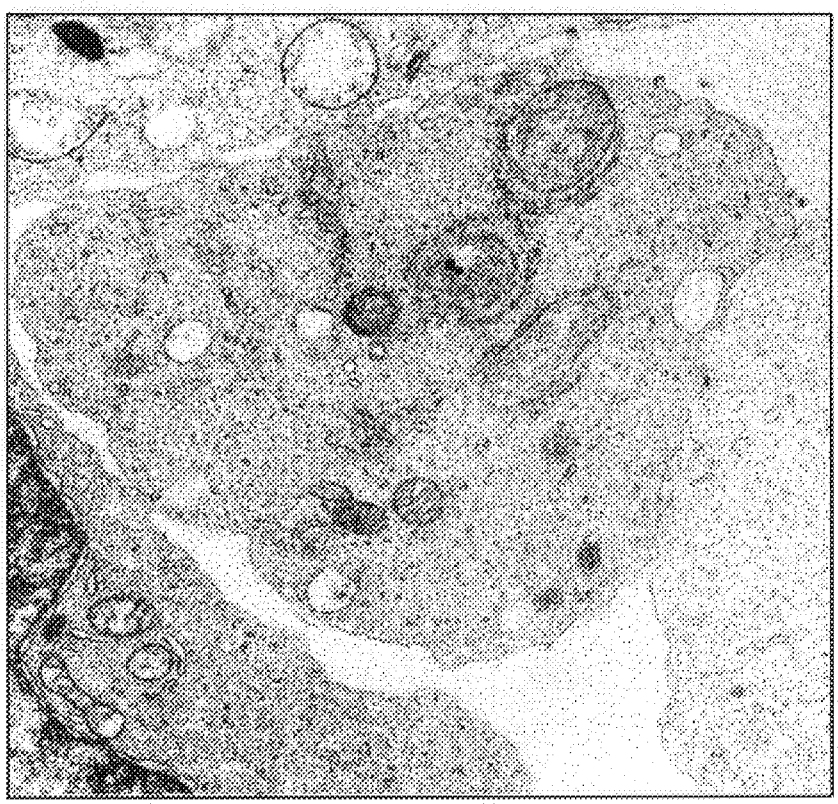
FIG. 11B evidences, for PMA-induced/mimosine-treated cells, the prominent reduction in the number of infectious particles in the extracellular space. Note that the ultrastructural appearance of the mimosine-treated cells at that time still lacks overt morphological signs of cell damage, such as altered mitochondria or disruption of the cytoplasmic membrane. Note, however, that such changes occur rapidly after withdrawal of the inhibitors (compare to time course detailed in FIGS. 12A and B and FIGS. 14A–H). [Magnification: 9100×].

As demonstrated in FIGS. 8A and B and 9A and B, using the infected H9 cell line, both hypusine inhibitors caused a marked dose-dependent, reduction of Gag-derived, intra- and extracellular p24 levels. In addition to this reduction in viral protein biosynthesis, the titration assays revealed a dramatic drop in the infectivity of virus as the concentration of each compound increased, declining by two orders of magnitude at a concentration of 500 μM. Using PMA-induced ACH-2 cells, this reduction in viral protein biosynthesis was confirmed for each hypusine inhibitor, as shown in FIG. 10 for the levels of the viral p24 protein. In contrast, the production and secretion of cellular TNF-α was not reduced but rather increased significantly, reaching levels in the supernatant of more than 100 pg/ml TNF-α under the experimental conditions employed, regardless of which compound was used. This observation suggests that the well-established, PMA-mediated induction of TNF-α synthesis [for example, Taylor et al., *J. Leukoc. Biol.* 54, 384–388 (1993), which is hereby incorporated by reference] is unaffected by hypusine inhibitors, whereas the PMA-mediated stimulation of HIV-1 production is susceptible to these agents. These findings argue for a selective suppressive effect of these compounds on HIV-1 replication. It is significant to note that in ACH-2 cells, TNF-A levels as low as 50 pg/ml induce a significant increase of HIV-1 expression [Folks et al. *Proc. Natl. Acad. Sci. USA* 86, 2365–2368 (1989), which is hereby incorporated by reference]. However, the observed increase in TNF-α levels was not sufficient to overcome the antiviral effect of the hypusine inhibitors (FIGS. 8A and B and 9A and B) and suggests that they abrogate not only the HIV-1-inducing effect of PMA, but also that of TNF-α. The selectivity of this antiviral effect was further corroborated by electron microscopic analysis. FIG. 11A, at a magnification of 9100×, shows three infected cells together with budding and mature HIV-1 particles; FIG. 11 B, representing the effect observed with mimosine, reveals a marked reduction in the number of viral particles in the presence of a normal ultrastructural appearance of the treated ACH-2 cells. In particular, the cytoplasmic, mitochondrial, and nuclear membranes are still well preserved, and the chromatin pattern is still unaltered in the majority of cells, although early apoptotic nuclear changes were noted in about 20% of cells. Similar results were obtained with the latently HIV-1-infected, PMA-inducible human cell line U1 which is derived not from human T-cells, but from the monocytic line U937 (data not shown).

B. Induction of apoptosis in virally-infected cells

Methods.

ACH-2 cells were incubated with hypusine inhibitors (mimosine, HK-1) and induced with PMA as outlined in Example II A, except that the duration of exposure to inhibitor was extended to 18–21 hours and that cells were labeled as detailed in Example I B. Half of the cells were then harvested and processed for detection of apoptosis, while the other half was washed free of inhibitors and re-incubated in fresh medium for 2–4 hours, followed by harvesting and processing for detection of 10 apoptosis. Using the same protocol, cultures of the parent CEM cell line were incubated in parallel. For assessment of apoptosis, cell viability was measured by exclusion of the dye trypan blue, by retention of the $^3$H-spermidine-derived intracellular radioactivity incorporated into the obligatory intracellular protein eIF-5A, and by direct fluorescence detection of the internucleosomal degradation of genomic DNA. Such irreversible genome degradation signals the activation of pre-programmed suicide mechanisms within any cell, which is the hallmark of apoptosis, and inescapably results in cell death [Compton, *Cancer Metast.* 11, 105–119 (1992), which is hereby incorporated by reference]. For the latter method, a commercially available kit was used (Oncor, Gaithersburg, Md.). Flow cytometric analysis of apoptotic cells was performed in accord with standard procedures.

Results.

Figure 12A:
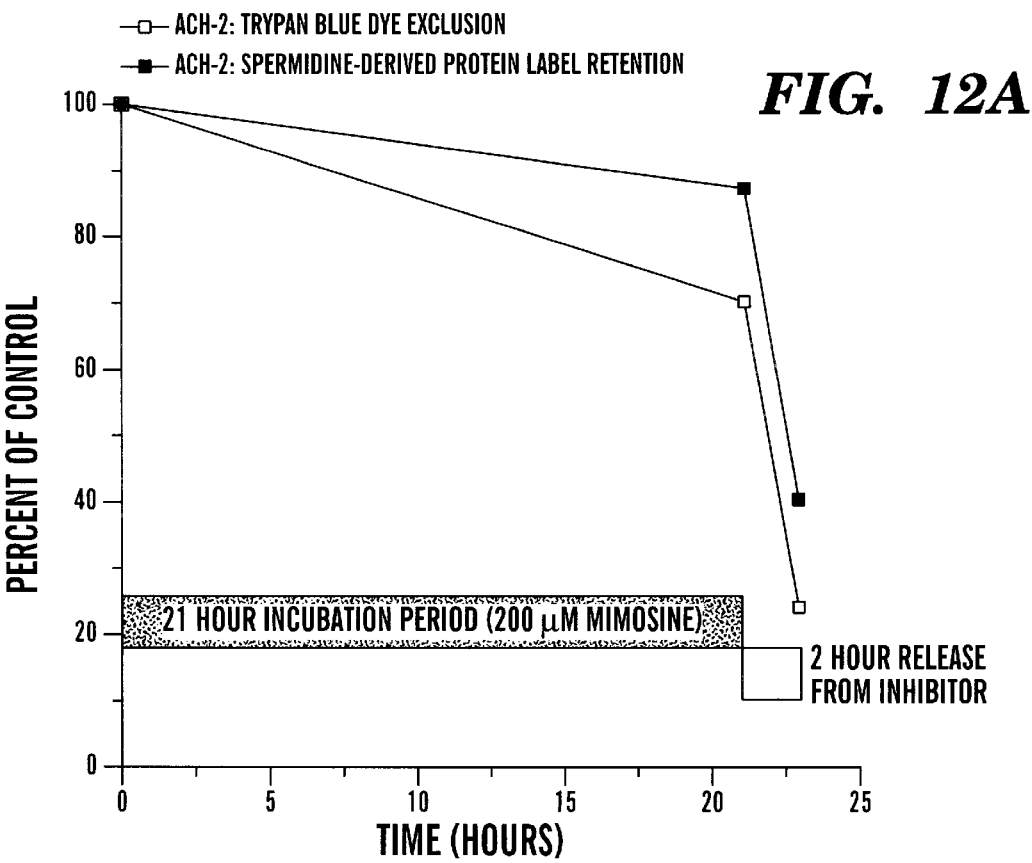
FIGS. 12A and B show the loss of cell membrane integrity suffered by HIV-1 producing ACH-2 cells and their uninfected parent cell line CEM during incubation with and after withdrawal of mimosine and HK-1. The black bar indicates the duration of inhibitor exposure, the open bar the duration of inhibitor withdrawal. Cell membrane integrity was determined by the ability of the cells to exclude the low-molecular weight dye trypan blue (FIGS. 12A and B) and to retain the spermidine-derived radioactive label of a single, obligatory intracellular protein species, eIF-5A and its deoxyhypusyl precursor (FIG. 12A). Consistent with the ultrastructural studies (compare FIGS. 11 A and B), the most marked, uniform and rapid decline of membrane integrity developed 2–4 hours after inhibitor withdrawal (FIGS. 12A and B). This effect showed remarkable selectivity for HIV-1 producing ACH-2 cells whereas in the uninfected CEM cells no such loss of membrane integrity was noted (FIG. 12B).
Figure 12B:
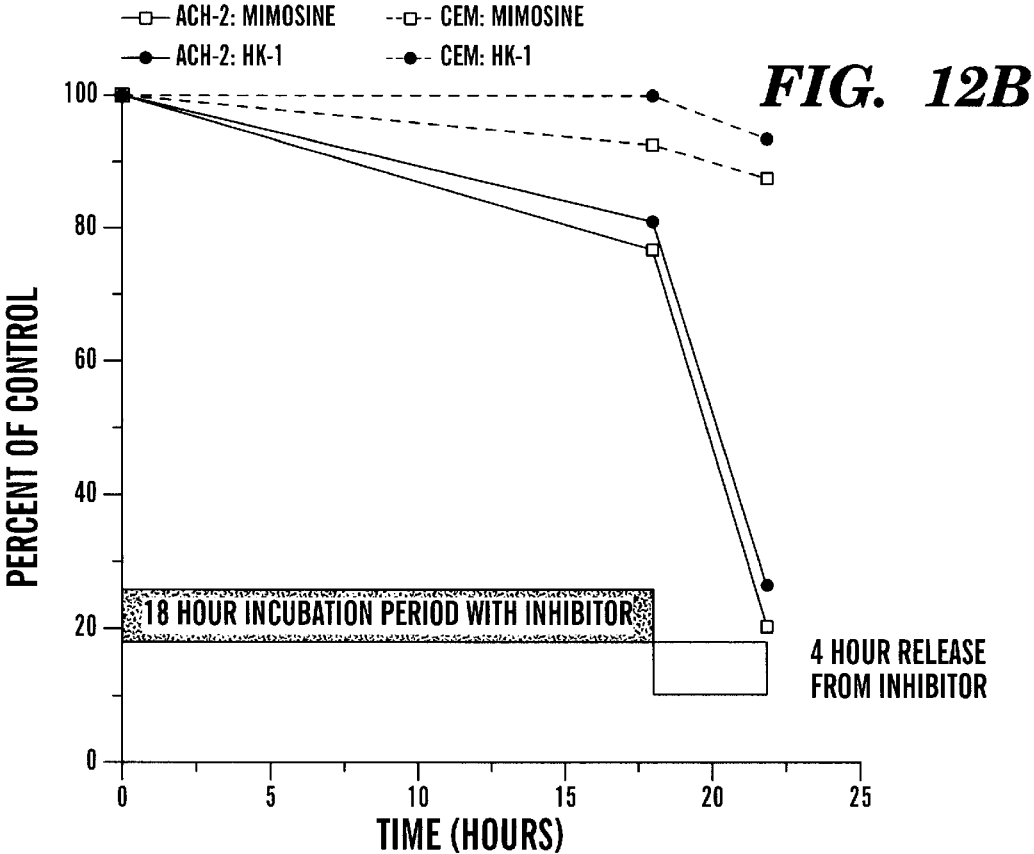
Figure 13A:
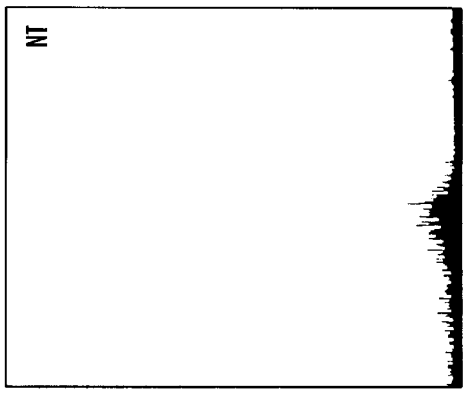
FIGS. 13A–F show the flowcytometrically determined distribution of the number of fluorescently labeled 3'-ends in the genomic DNA of HIV-1 producing ACH-2 cells ("ACH-2") and their uninfected parent cell line CEM ("CEM"), both receiving no treatment ("NT") or treatment for 18 hours with either 200 µM mimosine ("MIM") or 200 µM HK-1 ("HK1"). Only the virally-infected ACH-2, but not the parent CEM cells reacted to the inhibitors with a "shift to the right", i.e., with an increase of the number of 3'-ends in their DNA. This is the hallmark of irreversible auto-destruction of a cell's genetic library.
Figure 13B:
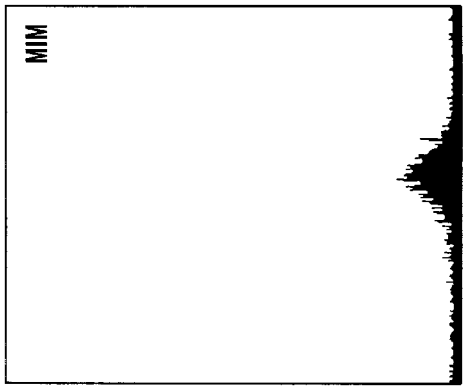
Figure 13C:
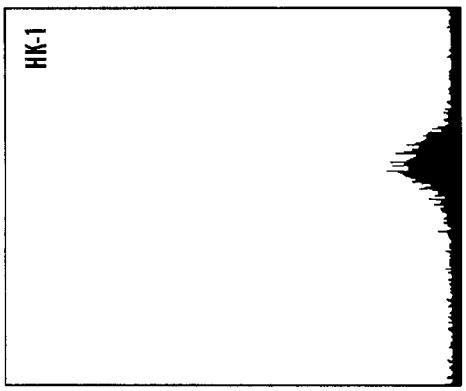
Figure 13D:
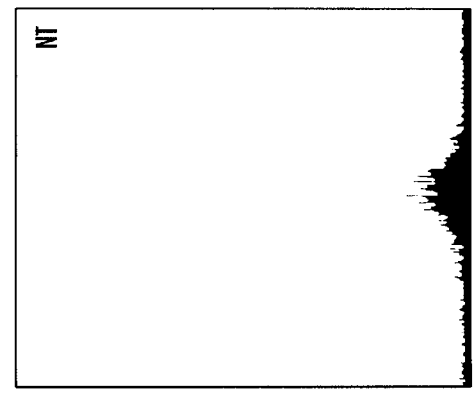
Figure 13E:
Figure 13F:
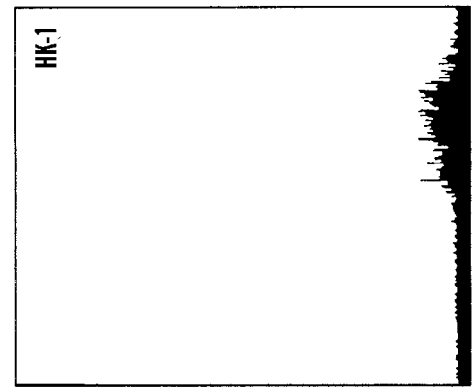
Figure 14A:
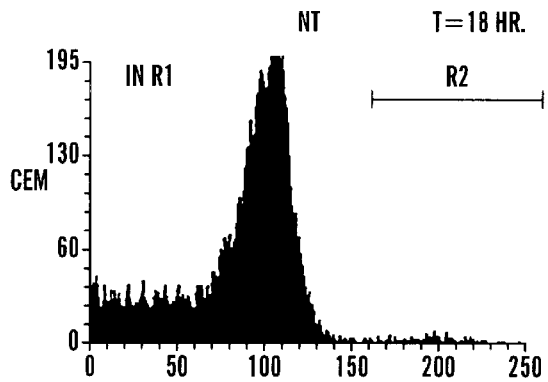
FIGS. 14A–H show the flowcytometrically determined distribution of the number of fluorescently labeled 3'-ends in the genomic DNA of HIV-1 producing ACH-2 cells ("ACH-2") and of their uninfected parent cell line CEM ("CEM"), both receiving no treatment ("NT") or treatment for 18 hours with 200 µM mimosine ("MIM"), followed by inhibitor withdrawal and reincubation in fresh medium for 2 hours. Only the virally infected ACH-2, but not the parent CEM cells reacted to the inhibitor with a "shift to the right", i.e., with an increase of the number of 3'-ends in their DNA. Within the 2 hours of release, this shift increased markedly, indicating rapid rise of irreversible auto-destruction upon discontinuation of the inhibitor. Note that the untreated CEM cells showed a significant population with genomic DNA 3'-ends below average frequency, as demonstrated by the "tail" extending to the left in the CEM "NT"-displays.
Figure 14E:
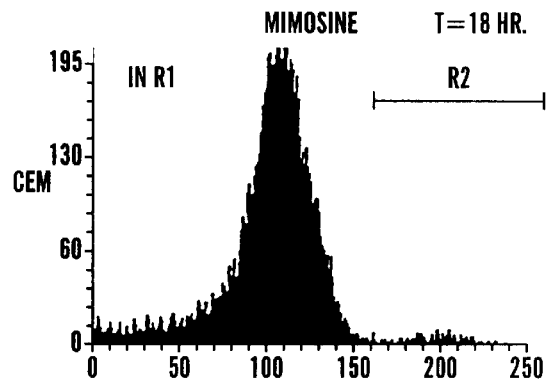
Figure 14B:
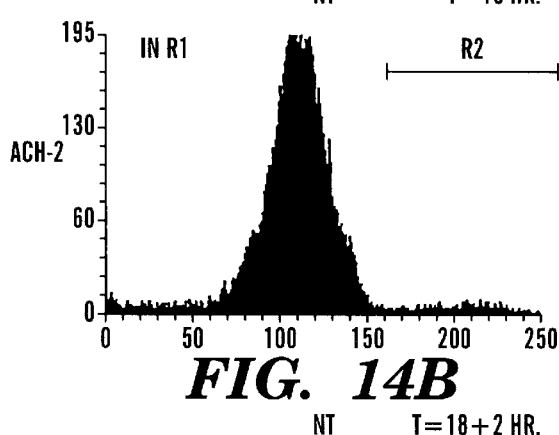
Figure 14F:
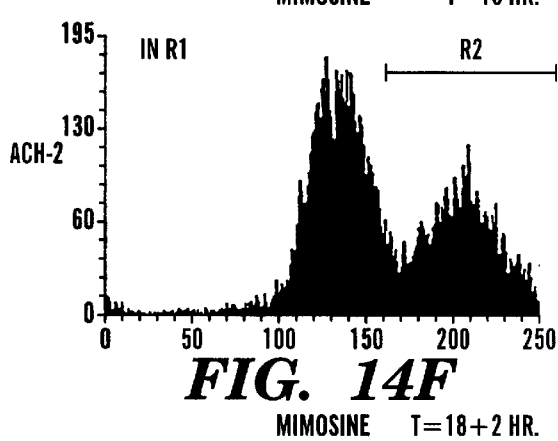
Figure 14C:
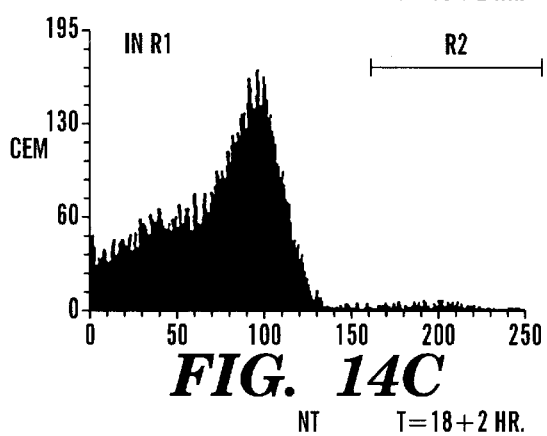
Figure 14G:
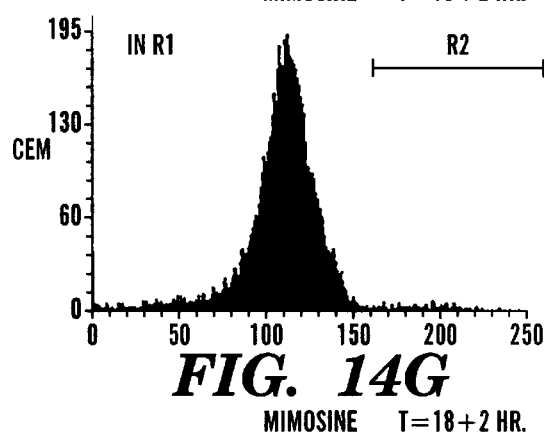
Figure 14D:
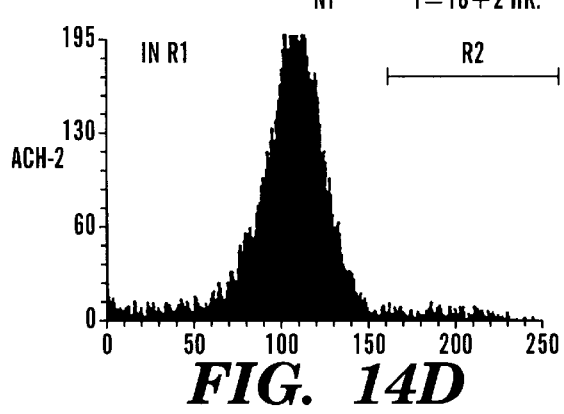
Figure 14H:
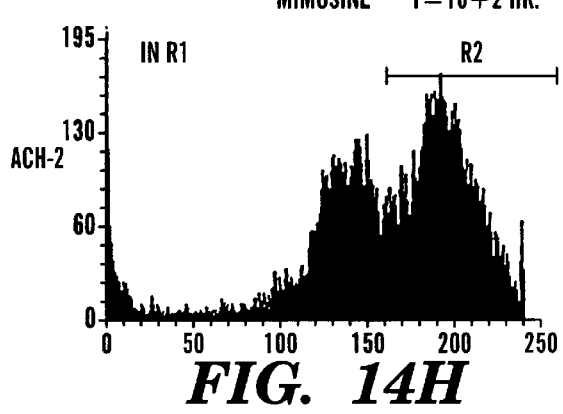

As demonstrated in FIGS. 12A and B, HIV-1 infected ACH-2 cells incubated with hypusine inhibitors developed a marked decline of their cell membrane integrity not during the extended period of exposure to the hypusine inhibitors but rather, such decline occurred rapidly after inhibitor removal; cell membrane integrity is defined as the ability both to retain intracellular non-secretory molecules, in this case measured as spermidine-derived protein label (i.e. eIF-5A and deoxyhypusyl precursor), and to exclude extracellular dye molecules, in this case trypan blue. Significantly, incubation with hypusine inhibitors followed by their removal did not affect the viability of the uninfected parent cell line CEM (FIG. 12B). Apparently, hypusine inhibitors caused suicidal differentiation of HIV-1 infected cells, i.e. such compounds triggered self-destructive mechanisms in these cells which became fully active upon their withdrawal. Flow cytometric investigations of untreated and inhibitor-treated ACH-2 and CEM cells revealed that hypusine inhibitors, particularly upon their removal, caused internucleosomal degradation of genomic DNA only in the virally-infected human cells, whereas the uninfected cells did not react with self-destruction. FIG. 13 shows that control CEM and ACH-2 cells, labeled NT, display a similarly positioned, distinct peak of apparently intact genomic DNA. An 18-hour exposure to 200 μM mimosine (MIM) or 200 μM HK-1 (HK1) did not affect the position of this peak in uninfected CEM cells. In infected ACH-2, however, both compounds triggered fragmentation of the genomic DNA as revealed by the broadening of the peak fluorescence and its 'shift to the right', resulting from the presence of an increased number of auto-destructively generated 3'-ends in the cellular DNA. The rapid increase in apoptosis upon withdrawal of the hypusine inhibitor is evidenced for mimosine in FIGS. 14A–H. Control cells, again labeled 'NT', displayed a marked peak of average fluorescence around channel 100 which directly reflected the amount of open 3'-ends of their DNA; the CEM cells actually showed a significant population of cells with less than the average number of such 3'-ends, as demonstrated by the 'tail' extending to the left in the CEM 'NT'-displays. Upon incubation and withdrawal of mimosine (200 $\mu$M), the position and shape of the average fluorescence peak in CEM cells did not change. In ACH-2 cells, however, the average fluorescence peak shifted upward to channel 140 after 18 hours of mimosine incubation, with concomittant emergence of a second population displaying an even higher amount of auto-destructively generated 3'-ends in their DNA and locating around channel 210. Within just 2 hours after mimosine withdrawal, this population did not decrease, but rather became the predominant one. At that time, the vast majority of the HIV-1—infected ACH-2 cells were in the process of committing suicide.

Although the invention has been described in detail for the purposes of illustration, it is understood that such detail is solely for that purpose, and variations can be made by those skilled in the art without departing from the spirit and scope of the invention that is defined by the following claims.

What is claimed:

1. A method of inhibiting intracellular synthesis of functional eIF-5A comprising:

administering, to eukaryotic cells, tissues, or individuals, an agent which blocks post-translational formation of hypusine in an amount sufficient to suppress biosynthesis of bioactive eIF-5A, wherein the agent is a deoxyhypusyl hydroxylase inhibitor other than mimosine comprising a compound of formulae I or II and derivatives thereof as follows:

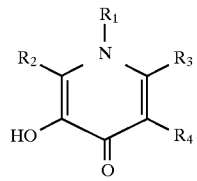

I

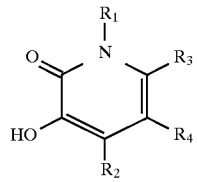

II $R_1$, $R_2$, $R_3$, and $R_4$ each individually represent a hydrogen, an alkyl, alkenyl, or alkoxy group containing 1 to about 8 carbon atoms an aryl aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

2. A method according to claim 1, wherein $R_2$ is H or an alkyl group with up to 2 carbon atoms and $R_3$ and $R_4$ are H or methyl.

3. A method according to claim 1, wherein $R_1$ and $R_2$ are methyl and $R_3$ and $R_4$ are H.

4. A method according to claim 1, wherein $R_1$ is $CH_2OCH_2CH_3$, $R_2$ is methyl, and $R_3$ and $R_4$ are H.

5. A method according to claim 1, wherein $R_1$ is $CH_2CH=CH_2$, $R_2$ is methyl, and $R_3$ and $R_4$ are H.

6. A method according to claim 1, wherein $R_1$ is ethyl, $R_2$ is methyl, and $R_3$ and $R_4$ are H.

7. A method according to claim 1, wherein $R_1$ is $(CH_2)_2CH_3$, $R_2$ is methyl, and $R_3$ and $R_4$ are H.

8. A method according to claim 1, wherein $R_1$, $R_2$, $R_3$, and/or $R_4$ is a peptide or peptidomimetic moiety.

9. A method of inhibiting translationally productive interaction of eIF-5A with viral elements of nucleic acid and/or protein structure comprising:

administering, to eukaryotic cells, tissues, or individuals, an agent which blocks intracellular hypusine formation in an amount sufficient to suppress the translationally productive interaction of eIF-5A with viral elements of nucleic acid and/or protein structure.

10. A method according to claim 9, wherein the agent comprises a compound of formulae I or II and derivatives thereof as follows:

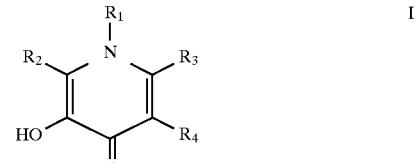

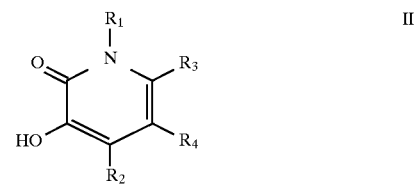

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

11. A method according to claim 10, wherein $R_2$ is H or an alkyl group with up to 2 carbon atoms and $R_3$ and $R_4$ are H or methyl.

12. A method according to claim 10, wherein $R_1$ is $CH_2CH(COOH)NH_2$ and $R_2$, $R_3$, and $R_4$ are H.

13. A method according to claim 12, wherein the compound is L-mimosine.

14. A method according to claim 10, wherein $R_1$ and $R_2$ are methyl and $R_3$ and $R_4$ are H.

15. A method according to claim 10, wherein $R_1$ is $CH_2OCH_2CH_3$, $R_2$ is methyl, and $R_3$ and $R_4$ are H.

16. A method according to claim 10, wherein $R_1$ is $CH_2CH=CH_2$, $R_2$ is methyl, and $R_3$ and $R_4$ are H.

17. A method according to claim 10, wherein $R_1$ is ethyl, $R_2$ is methyl, and $R_3$ and $R_4$ are H.

18. A method according to claim 10, wherein $R_1$ is $(CH_2)_2CH_3$, $R_2$ is methyl, and $R_3$ and $R_4$ are H.

19. A method according to claim 10, wherein $R_1$, $R_2$, $R_3$, and/or $R_4$ is a peptide or peptidomimetic moiety.

20. A method of inhibiting biosynthesis of viral proteins of Rev-dependent lentiviruses or of viruses dependent on interaction of eIF-5A with viral elements of nucleic acid and/or protein structure comprising:

administering, to eukaryotic cells, tissues, or individuals, an agent which blocks intracellular hypusine formation in an amount sufficient to inhibit biosynthesis of viral proteins of Rev-dependent lentiviruses or of viruses dependent on interaction of eIF-5A with viral elements of nucleic acid and/or protein structure.

21. A method according to claim 20, wherein the agent comprises a compound of formulae I or II and derivatives thereof as follows:

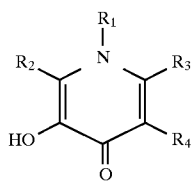

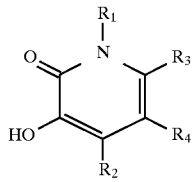

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

22. A method according to claim 21, wherein $R_2$ is H or an alkyl group with up to 2 carbon atoms and $R_3$ and $R_4$ are H or methyl.

23. A method according to claim 21, wherein $R_1$ is $CH_2CH(COOH)NH_2$ and $R_2$, $R_3$, and $R_4$ are H.

24. A method according to claim 23, wherein the compound is L-mimosine.

25. A method according to claim 21, wherein $R_1$ and $R_2$ are methyl and $R_3$ and $R_4$ are H.

26. A method according to claim 21, wherein $R_1$ is $CH_2OCH_2CH_3$, $R_2$ is methyl, and $R_3$ and $R_4$ are H.

27. A method according to claim 21, wherein $R_1$ is $CH_2CH=CH_2$, $R_2$ is methyl, and $R_3$ and $R_4$ are H.

28. A method according to claim 21, wherein $R_1$ is ethyl, $R_2$ is methyl, and $R_3$ and $R_4$ are H.

29. A method according to claim 21, wherein $R_1$ is $(CH_2)_2CH_3$, $R_2$ is methyl, and $R_3$ and $R_4$ are H.

30. A method according to claim 21, wherein $R_1$, $R_2$, $R_3$, and/or $R_4$ is a peptide or peptidomimetic moiety.

31. A method of inhibiting replication of Rev-dependent lentiviruses or viruses dependent on interaction of eIF-5A with viral elements of nucleic acid and/or protein structure comprising:

administering, to eukaryotic cells, tissues, or individuals, an agent which blocks intracellular hypusine formation in an amount sufficient to inhibit replication of Rev-dependent lentiviruses or of viruses dependent on interaction of eIF-5A with viral elements of nucleic acid and/or protein structure.

32. A method according to claim 31, wherein the agent comprises a compound of formulae I or II and derivatives thereof as follows:

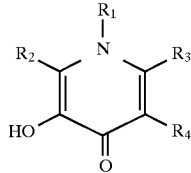

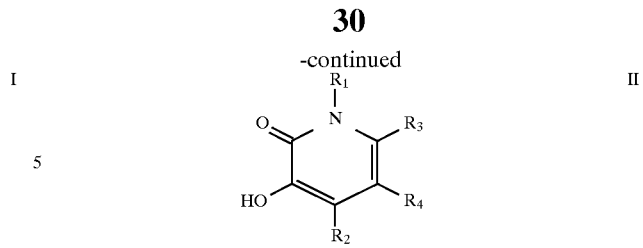

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

33. A method according to claim 32, wherein $R_2$ is H or an alkyl group with up to 2 carbon atoms and $R_3$ and $R_4$ are H or methyl.

34. A method according to claim 32, wherein $R_1$ is $CH_2CH(COOH)NH_2$ and $R_2$, $R_3$, and $R_4$ are H.

35. A method according to claim 33, wherein the compound is L-mimosine.

36. A method according to claim 32, wherein $R_1$ and $R_2$ are methyl and $R_3$ and $R_4$ are H.

37. A method according to claim 32, wherein $R_1$ is $CH_2OCH_2CH_3$, $R_2$ is methyl, and $R_3$ and $R_4$ are H.

38. A method according to claim 32, wherein $R_1$ is $CH_2CH=CH_2$, $R_2$ is methyl, and $R_3$ and $R_4$ are H.

39. A method according to claim 32, wherein $R_1$ is ethyl, $R_2$ is methyl, and $R_3$ and $R_4$ are H.

40. A method according to claim 32, wherein $R_1$ is $(CH_2)_2CH_3$, $R_2$ is methyl, and $R_3$ and $R_4$ are H.

41. A method according to claim 32, wherein $R_1$, $R_2$, $R_3$, and/or R4 is a peptide or peptidomimetic moiety.

42. A method according to claim 31, wherein said method is for treating an individual infected with an eIF-5A-dependent virus and said administering involves administering to the individual an effective amount of the agent.

43. A method according to claim 42, wherein said administering is carried out topically or systemically.

44. A method according to claim 43, wherein said administering is carried out by percutaneous, oral, intravascular, intramuscular, intraperitoneal, intrathecal, or subcutaneous application, or ocular and mucous membrane administration.

45. A method according to claim 42, wherein the agent is administered with a physiologically suitable carrier.

46. A method according to claim 31, wherein the Rev-dependent lentivirus or virus dependent on interaction of host cell eIF-5A with viral elements of nucleic acid and/or protein structure is selected from the group consisting of human T-cell leukemia viruses, human immunodeficiency viruses, hepatitis B virus, simian immunodeficiency viruses, the bovine immunodeficiency viruses, feline immunodeficiency viruses, visna virus, equine infectious anemia virus, caprine arthritis-encephalitis virus, and Mason-Pfizer virus.

47. A method according to claim 31, wherein the Rev-dependent lentivirus or virus dependent on interaction of host cell eIF-5A with viral elements of nucleic acid and/or protein structure is a human immunodeficiency virus.

48. A method according to claim 31, wherein said administering induces apoptosis of cells infected with pathogenic viral particles employing Rev or dependent on interaction of host cell eIF-5A with viral elements of nucleic acid and/or protein structure.

49. A method according to claim 48, further comprising:
withdrawing said agent from the eukaryotic cells, tissues, or individuals to enhance apoptosis of cells infected with pathogenic viral particles employing Rev or dependent on interaction of host cell eIF-5A with viral elements of nucleic acid and/or protein structure.

50. A method of inducing apoptosis in cells infected with Rev-dependent lentiviruses or viruses dependent on interaction of eIF-5A with viral elements of nucleic acid and/or protein structure comprising:

administering, to cells infected with Rev-dependent lentiviruses or viruses dependent on interaction of host cell eIF-5A with viral elements of nucleic acid and/or protein structure, an agent which blocks intracellular hypusine formation in an amount sufficient to induce apoptosis of virally-infected cells.

51. A method according to claim 50, further comprising:

withdrawing said agent from the cells to enhance apoptosis of cells infected with pathogenic viral particles employing Rev or viruses dependent on interaction of host cell eIF-5A with viral elements of nucleic acid and/or protein structure.

52. A method according to claim 50, wherein the agent comprises a compound of formulae I or II and derivatives thereof as follows:

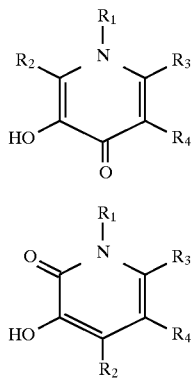

$R_1$, $R_2$, $R_3$, and $R_4$ each individually represent a hydrogen, an alkyl, alkenyl, or alkoxy group containing 1 to about 8 carbon atoms, an aryl, aralkyl, or cycloalkyl group containing about 5 to 12 carbon atoms, or a carboalkoxy or carbamyl group containing up to 8 carbon atoms, or a peptide or peptidomimetic moiety containing 10 to about 30 carbon atoms.

53. A method according to claim 52 wherein $R_2$ is H or an alkyl group with up to 2 carbon atoms and $R_3$ and $R_4$ are H or methyl.

54. A method according to claim 52, wherein $R_1$ is $CH_2CH(COOH)NH_2$ and $R_2$, $R_3$, and $R_4$ are H.

55. A method according to claim 54, wherein the compound is L-mimosine.

56. A method according to claim 55, wherein $R_1$ and $R_2$ are methyl and $R_3$ and $R_4$ are H.

57. A method according to claim 52, wherein $R_1$ is $CH_2OCH_2CH_3$, $R_2$ is methyl, and $R_3$ and $R_4$ are H.

58. A method according to claim 52, wherein $R_1$ is $CH_2CH=CH_2$, $R_2$ is methyl, and $R_3$ and $R_4$ are H.

59. A method according to claim 52, wherein $R_1$ is ethyl, $R_2$ is methyl, and $R_3$ and $R_4$ are H.

60. A method according to claim 52, wherein $R_1$ is $(CH_2)_2CH_3$, $R_2$ is methyl, and $R_3$ and $R_4$ are H.

61. A method according to claim 52, wherein $R_1$, $R_2$, $R_3$, and/or $R_4$ is a peptide or peptidomimetic moiety.

* * * * *

UNITED STATES PATENT AND TRADEMARK OFFICE
CERTIFICATE OF CORRECTION

PATENT NO. : 5,849,587
DATED : December 15, 1998
INVENTOR(S) : Hanauske et al.

Page 1 of 1

It is certified that error appears in the above-identified patent and that said Letters Patent is hereby corrected as shown below:

On title page,
Under heading [73] Assignee, the following text should be added: --; New York Blood Center, New York, N.Y.

Signed and Sealed this

Seventeenth Day of July, 2001

*Attest:*

Nicholas P. Godici

NICHOLAS P. GODICI
*Acting Director of the United States Patent and Trademark Office*

*Attesting Officer*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

A T A A T C C A C C     T A T C C C A G T A     G G A                        2 3

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

T T T G G T C C T T     G T C T T A T G T C     C A G A A T G                2 7

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

C A A A G T T G T C     A T G G A T G A C C                               2 0

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (ii) MOLECULE TYPE: cDNA (xi) SEQUENCE DESCRIPTION: SEQ ID NO:4:

CCATGGAGAA GGCTGGGG                                                                 18